United States Patent
Pal et al.

(10) Patent No.: US 12,020,811 B2
(45) Date of Patent: Jun. 25, 2024

(54) SYSTEMS AND METHODS FOR TECHNICAL SUPPORT OF CONTINUOUS ANALYTE MONITORING AND SENSOR SYSTEMS

(71) Applicant: Dexcom, Inc., San Diego, CA (US)

(72) Inventors: Andrew Attila Pal, San Diego, CA (US); Leif N. Bowman, San Diego, CA (US); Eric Cohen, San Diego, CA (US); Basab Dattaray, San Diego, CA (US); Edward Day, Dania Beach, FL (US); Apurv Ullas Kamath, San Diego, CA (US); Aarthi Mahalingam, San Diego, CA (US); Dana Denea Minor, Oceanside, CA (US); Scott A. Moss, Encinitas, CA (US); Neil S. Puri, La Jolla, CA (US); Eli Reihman, San Diego, CA (US); Conrad Woods, San Diego, CA (US); Laurie L. Berg, Carlsbad, CA (US); Jorge Valdes, Solana Beach, CA (US)

(73) Assignee: Dexcom, Inc., San Diego, CA (US)

( * ) Notice: Subject to any disclaimer, the term of this patent is extended or adjusted under 35 U.S.C. 154(b) by 31 days.

(21) Appl. No.: 17/937,412

(22) Filed: Sep. 30, 2022

(65) Prior Publication Data
US 2023/0027200 A1 Jan. 26, 2023

Related U.S. Application Data

(63) Continuation of application No. 15/806,078, filed on Nov. 7, 2017, now Pat. No. 11,462,320, which is a
(Continued)

(51) Int. Cl.
*G16H 40/40* (2018.01)
*A61B 5/00* (2006.01)
(Continued)

(52) U.S. Cl.
CPC .......... *G16H 40/40* (2018.01); *A61B 5/0002* (2013.01); *A61B 5/0015* (2013.01);
(Continued)

(58) Field of Classification Search
CPC ................................. G06Q 50/20–26
See application file for complete search history.

(56) References Cited

U.S. PATENT DOCUMENTS 6,001,067 A 12/1999 Shults et al.
6,424,847 B1 7/2002 Mastrototaro et al.
(Continued)

FOREIGN PATENT DOCUMENTS

EP 2327984 A2 6/2011
JP 108286779 A 11/1996
(Continued)

OTHER PUBLICATIONS

Mossman, Insulin pumps: design basics and trade-offs, Jun. 14, 2010, Electronic Engineering Times, pp. 48-52. (Year: 2010).
(Continued)

*Primary Examiner* — Neal Sereboff
(74) *Attorney, Agent, or Firm* — Patterson + Sheridan, LLP

(57) ABSTRACT

Disclosed are systems and methods for providing automated or semi-automated technical support for patients using medical devices, such as continuous glucose monitoring systems. Disclosed embodiments of automated tech support system include collection and storage of copies of streams of medical device data on multiple servers, analysis and comparison of data streams, remote tech support initiation and usage of the automated tech support system for providing improved products and services by storing and analyzing historical tech support data.

17 Claims, 10 Drawing Sheets

Related U.S. Application Data continuation of application No. 15/805,677, filed on Nov. 7, 2017, now Pat. No. 11,295,855.

(60) Provisional application No. 62/419,900, filed on Nov. 9, 2016.

(51) Int. Cl.

| | | |
|---|---|---|
| *A61B 5/145* | (2006.01) | |
| *G06F 16/951* | (2019.01) | |
| *G16H 40/67* | (2018.01) | |
| *G16H 50/30* | (2018.01) | |

(52) U.S. Cl.
CPC ...... *A61B 5/14532* (2013.01); *A61B 5/14546* (2013.01); *G06F 16/951* (2019.01); *G16H 40/67* (2018.01); *G16H 50/30* (2018.01)

(56) References Cited

U.S. PATENT DOCUMENTS

| | | | |
|---|---|---|---|
| 6,477,395 | B2 | 11/2002 | Schulman et al. |
| 6,484,046 | B1 | 11/2002 | Say et al. |
| 6,512,939 | B1 | 1/2003 | Colvin et al. |
| 6,565,509 | B1 | 5/2003 | Say et al. |
| 6,579,690 | B1 | 6/2003 | Bonnecaze et al. |
| 6,931,327 | B2 | 8/2005 | Goode, Jr. et al. |
| 7,310,544 | B2 | 12/2007 | Brister et al. |
| 7,946,985 | B2 | 5/2011 | Mastrototaro et al. |
| 8,423,113 | B2 | 4/2013 | Shariati et al. |
| 9,172,705 | B1 | 10/2015 | Kong et al. |
| 9,282,925 | B2 * | 3/2016 | Kamath ................ A61B 5/725 |
| 9,804,150 | B2 | 10/2017 | Hayter et al. |
| 10,646,650 | B2 | 5/2020 | Cinar et al. |
| 2005/0027463 | A1 | 2/2005 | Goode, Jr. et al. |
| 2005/0043598 | A1 | 2/2005 | Goode, Jr. et al. |
| 2005/0154271 | A1 | 7/2005 | Rasdal et al. |
| 2005/0192557 | A1 | 9/2005 | Brauker et al. |
| 2005/0203360 | A1 | 9/2005 | Brauker et al. |
| 2006/0020187 | A1 | 1/2006 | Brister et al. |
| 2006/0222566 | A1 | 10/2006 | Brauker et al. |
| 2007/0016381 | A1 | 1/2007 | Kamath et al. |
| 2007/0027385 | A1 | 2/2007 | Brister et al. |
| 2007/0032706 | A1 | 2/2007 | Kamath et al. |
| 2007/0032733 | A1 | 2/2007 | Burton |
| 2007/0197890 | A1 | 8/2007 | Boock et al. |
| 2007/0203966 | A1 | 8/2007 | Brauker et al. |
| 2007/0208245 | A1 | 9/2007 | Brauker et al. |
| 2007/0208246 | A1 | 9/2007 | Brauker et al. |
| 2008/0033254 | A1 | 2/2008 | Kamath et al. |
| 2008/0108942 | A1 | 5/2008 | Brister et al. |
| 2008/0119703 | A1 | 5/2008 | Brister et al. |
| 2009/0043525 | A1 * | 2/2009 | Brauker ............ A61M 5/1723 702/179 |
| 2009/0057148 | A1 | 3/2009 | Wieder et al. |
| 2009/0192366 | A1 * | 7/2009 | Mensinger ............ G16H 40/63 706/14 |
| 2009/0240120 | A1 | 9/2009 | Mensinger et al. |
| 2009/0275805 | A1 | 11/2009 | Lane et al. |
| 2010/0179409 | A1 * | 7/2010 | Kamath ................ A61B 5/725 702/19 |
| 2010/0265073 | A1 | 10/2010 | Harper |
| 2010/0292544 | A1 * | 11/2010 | Sherman ............ A61M 16/101 128/204.23 |
| 2012/0310050 | A1 | 12/2012 | Osorio |
| 2013/0076531 | A1 * | 3/2013 | San Vicente ......... A61B 5/0015 340/870.02 |
| 2013/0267809 | A1 | 10/2013 | Brister et al. |
| 2013/0303869 | A1 | 11/2013 | Rebec et al. |
| 2013/0337571 | A1 | 12/2013 | Mizuoka et al. |
| 2014/0012511 | A1 | 1/2014 | Mensinger et al. |
| 2014/0184422 | A1 | 7/2014 | Mensinger et al. |
| 2014/0187889 | A1 | 7/2014 | Cohen et al. |
| 2014/0207400 | A1 | 7/2014 | Hayter et al. |
| 2015/0199489 | A1 | 7/2015 | Muradia |
| 2015/0226752 | A1 * | 8/2015 | Nazareth ................ G01N 33/76 422/403 |
| 2015/0374299 | A1 | 12/2015 | Hayter |
| 2016/0021169 | A1 | 1/2016 | Chan |
| 2016/0120448 | A1 | 5/2016 | Hernandez-Rosas et al. |
| 2016/0217472 | A1 | 7/2016 | Podgorny et al. |
| 2016/0227361 | A1 * | 8/2016 | Booth .................. H04W 4/029 |
| 2016/0346459 | A1 * | 12/2016 | Chow .................. A61M 5/145 |
| 2016/0354543 | A1 * | 12/2016 | Cinar .................. G16H 40/63 |
| 2017/0007129 | A1 | 1/2017 | Kaib et al. |
| 2017/0367631 | A1 | 12/2017 | Reggiardo et al. |
| 2018/0103879 | A1 | 4/2018 | Masciotti et al. |
| 2018/0129784 | A1 | 5/2018 | Pal et al. |
| 2018/0129785 | A1 | 5/2018 | Pal et al. |
| 2018/0286510 | A1 | 10/2018 | Kwan et al. |
| 2019/0216373 | A1 | 7/2019 | Harper |
| 2020/0178868 | A1 | 6/2020 | Mueller et al. |
| 2020/0205694 | A1 | 7/2020 | Bohm et al. |

FOREIGN PATENT DOCUMENTS

| | | |
|---|---|---|
| WO | 2010127051 A1 | 11/2010 |
| WO | 2010146579 A1 | 12/2010 |

OTHER PUBLICATIONS

International Search Report and Written Opinion for Application No. PCT/US2022/075862, dated Nov. 17, 2022, 13 pages.

International Preliminary Report on Patentability for Application No. PCT/US2017/060440 dated May 23, 2019, 6 pages.

International Search Report and Written opinion for Application No. PCT/US2017/060440 dated Feb. 1, 2018, 6 pages.

Marling C., et al., "Emerging Applications for Intelligent Diabetes Management," 2012, AI Magazine, pp. 67-78.

* cited by examiner

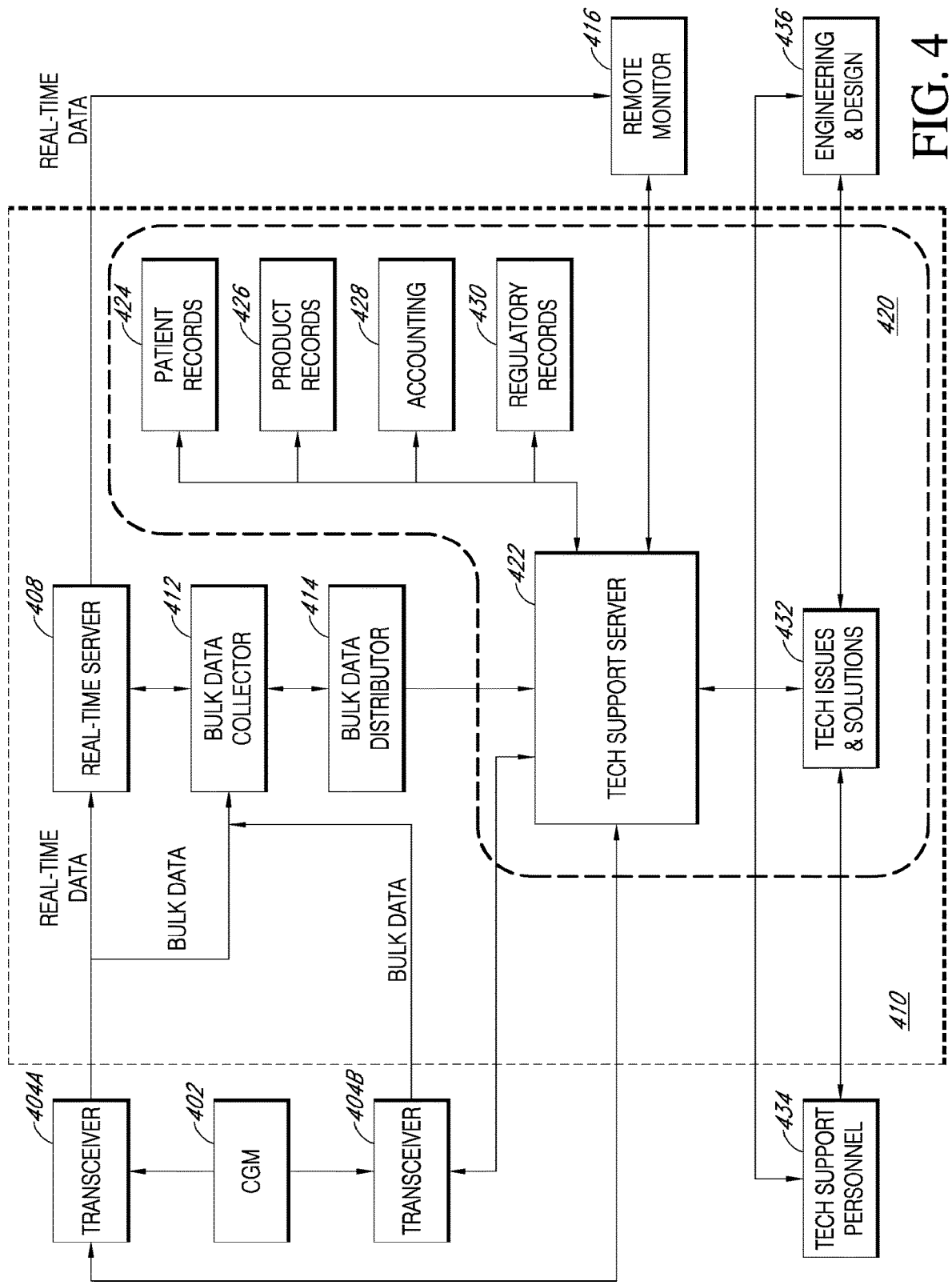

SYSTEMS AND METHODS FOR TECHNICAL SUPPORT OF CONTINUOUS ANALYTE MONITORING AND SENSOR SYSTEMS

CROSS-REFERENCE TO RELATED APPLICATIONS

This application is a continuation of U.S. patent application Ser. No. 15/806,078, filed Nov. 7, 2017, which is a continuation of U.S. patent application Ser. No. 15/805,677, filed Nov. 7, 2017, issued as U.S. Pat. No. 11,295,855, which claims priority to and benefit of U.S. Provisional Patent Application No. 62/419,900, filed Nov. 9, 2016. Each of the aforementioned applications is incorporated by reference herein in its entirety, and each is hereby expressly made a part of this specification.

TECHNICAL FIELD

The present disclosure relates generally to automated or semi-automated technical support of medical device systems. More particularly, the present disclosure is directed to systems, methods, apparatuses, and computer products for automated or semi-automated technical support of a continuous analyte monitoring system.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

For example, diabetic patients sample their blood glucose levels several times throughout a day, such as in the morning, around lunch, and in the evening. The levels can be measured by taking a small blood sample of the patient and measuring the glucose levels with a test strip or glucose meter. This technique, however, has drawbacks because patients would prefer to not have to take a blood sample, and users do not know what their blood glucose levels are throughout the day between the samples.

Consequently, a variety of non-invasive, transdermal (e.g., transcutaneous) and/or implantable electrochemical sensors have been and are being developed for continuously detecting and/or quantifying glucose values, such as from sensor measurements having accuracy corresponding to direct blood glucose measurements. Continuous glucose monitors have been increasing in popularity as an easy way to monitor glucose levels and automatically alert the patient of glucose level events. For example, one potentially dangerous timeframe is at night because a patient's glucose levels can fall dangerously low during sleep. As a result, continuous glucose monitors have gained popularity by providing a sensor that continuously measures glucose levels of a patient and transmits the measured glucose levels wirelessly to a display. This allows the patient or patient's caregiver to monitor the patient's glucose levels throughout the day and even set alarms for when glucose levels reach a predefined level or experience a defined change.

Initially, continuous glucose monitors wirelessly transmitted data relating to glucose levels to a dedicated display. The dedicated display is a medical device designed to display glucose levels, trending patterns, and other information for a user. However, with the increasing popularity of smart phones and software applications (apps) executing on smart phones, some users prefer to avoid having to carry a dedicated display. Instead, some users prefer to monitor their glucose levels using a dedicated software app executing on their mobile computing device, such as a smart phone, tablet or wearable device like a smartwatch or smart glasses.

SUMMARY

One embodiment includes a system, wherein the system includes: a continuous analyte sensor device configured to sense one or more biological parameters of a patient user, generate real time medical data and bulk data, and selectively transmit the real time medical data and bulk data; a real time server configured to receive and store the real time medical data; a bulk data server configured to receive and store the bulk data; and a tech support server configured to identify a technical issue associated with the continuous analyte sensor device, at least in part by analysis of the stored real time medical data and the bulk data.

In one aspect, the analysis of the real time medical data and the bulk data includes a comparison of the real time medical data and the bulk data to determine discrepancies.

In another aspect, the system further includes a remote monitor device operated by a caregiver user affiliated with the patient user, the remote monitor device configured to receive the real time medical data and/or alerts associated with the real time medical data from the real time server, and to transmit an issue report indicative of the technical issue to the tech support server.

In another aspect, the system further includes one or more recording databases, wherein the tech support server is configured to modify the one or more recording databases in response to the identification of the technical issue.

In another aspect, the recording databases includes a regulatory incident records database.

In another aspect, the system further includes an engineering and design computing system configured to receive alerts or reports comprising the identified technical issue.

In another aspect, the reports or alerts comprise trends in emerging technical issues.

In one aspect, the tech support server is further configured to search for a resolution of the identified technical issue, resolve the identified technical issue and notify the patient user.

In one aspect, the system further includes a tech knowledge database, wherein searching for a resolution of the identified issue comprises querying the tech knowledge database.

In another aspect, the tech knowledge database further comprises a mapping of technical issues, known resolutions and scores associated with the known resolutions.

In one aspect, the tech knowledge database is routinely purged of low score resolutions.

In one aspect, the system further includes a transceiver configured to selectively receive the real time medical data and bulk data, transmit the data to the real time server, the bulk data server or both; and an application running on the transceiver configured to gather data related to the technical issue, generate and transmit an error ticket containing the technical issue and the gathered data to the tech support server.

In another aspect, the system is further configured to gather data based on patient inputs related to the technical issue.

In one aspect, the system further includes a tech support personnel computing system, configured to receive the identified technical issue and a report of the tech support server related to the identified technical issue.

In another aspect, the technical issue comprises a sensor failure and the tech support server is configured to order a replacement sensor and provide tracking information to the patient user.

Another embodiment includes a method where the method includes: sensing one or more biological parameters of a patient user; generating real time medical data and bulk data from at least the sensed one or more biological parameters; transmitting the real time medical data to a real time server; storing the real time medical data in the real time server; transmitting the bulk data to a bulk data server; storing the bulk data in the bulk data server; and identifying a technical issue at least in part by analysis of the real time medical data and the bulk data.

In one aspect of the method, the analysis of the real time medical data and the bulk data includes a comparison of the real time medical data and the bulk data to determine discrepancies.

In one aspect, the method further includes transmitting, from the real time server, the real time medical data to a remote monitor device operated by a caregiver user affiliated with the patient user, the remote monitor device configured to receive the real time medical data and/or alerts associated with the real time medical data; and receiving, at the tech support server, an issue report indicative of the technical issue to a tech support server.

In another aspect, the method further includes modifying one or more recording databases in response to the identified technical issue.

In another aspect, the one or more recording databases comprise a regulatory incident records database.

In one aspect, the method further includes transmitting alerts or reports to an engineering and design computing system.

In another aspect, the reports or alerts comprise trends in emerging technical issues.

In one aspect, the method further includes searching for a resolution of the identified technical issue, resolving the identified technical issue and notifying the patient user.

In one aspect, searching for a resolution includes querying a tech knowledge database.

In another aspect, the tech knowledge database further comprises a mapping of technical issues, known resolutions and scores associated with the known resolutions.

In one aspect, the method further includes routinely purging the tech knowledge database of low score resolutions.

In another aspect, the method further includes: gathering data related to the technical issue; and generating and transmitting an error ticket containing the technical issue and the gathered data to a tech support server.

In one aspect, the method further includes gathering data based on patient inputs related to the technical issue.

In another aspect, the method further includes sending the identified technical issue and a report of the tech support server to a tech support personnel computing system.

In one aspect, the method further includes ordering a replacement sensor and providing tracking information to the patient user in response to the identified technical issue.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

FIG. 4 illustrates an example architecture of an automated or semi-automated technical support system in accordance with embodiments of the present technology.

Figure 1A:
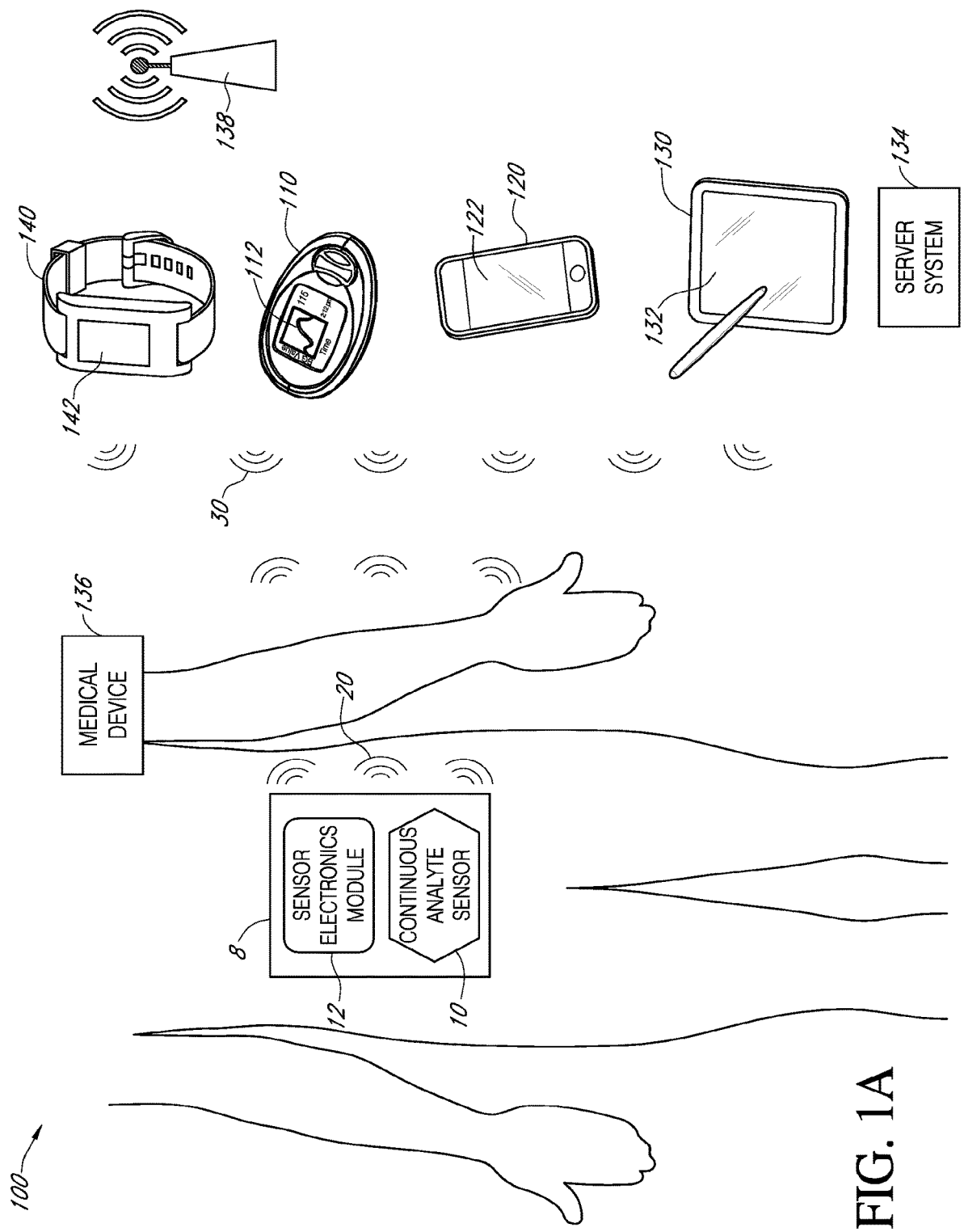
FIG. 1A illustrates aspects of an example system that may be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

The convenience and added safety of using modern continuous glucose monitoring systems have led to an increase in the number of diabetes patients using such systems. With increased usage, the patients' need for efficient technical support has also increased. Providing technical support of medical devices often entails compliance with government regulatory regimes directed to these devices. For example, medical device providers are sometimes under an obligation to track and record data related to detection and resolution of technical issues encountered by patients. Additionally, a modern medical device provider has its internal systems and procedures that may be triggered with each patient request for technical support. As patient population utilizing modern medical devices increases, so does the volume of patients requesting tech support. In some cases, conventional methods of providing medical device customer server are not efficient or not easily scalable to meet the increased demands. Consequently, there is a need for automated or semi-automated technical support systems to provide improved and efficient technical support to users of modern medical devices and associated infrastructure.

Embodiments of the present disclosure are directed to systems, methods, and devices for providing automated or semi-automated technical support solutions in a government regulated medical device system and infrastructure context. In various deployments described herein, the analyte data is glucose data generated by an analyte sensor system configured to connect to display devices and the like. Implementing aspects of the present disclosure, as described in detail herein, can establish systems and methods capable of providing automated or semi-automated technical support for a government-regulated medical device. In particular, such aspects of the disclosure relate to enabling remote initiation of a request for automatic tech support, performing government-compliant recording of a tech support incident and enabling alerts or reports to internal departments within a medical device provider to improve medical device products and services.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

Overview

In some embodiments, a system is provided for continuous measurement of an analyte in a host. The system may include: a continuous analyte sensor configured to continuously measure a concentration of the analyte in the host, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, and/or reaction products. In some implementations, the analyte for measurement by the methods or devices is glucose. However, other analytes are contemplated as well, including but not limited to: acarboxyprothrombin; acetoacetic acid; acetone; Acetyl CoA; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; ketone bodies; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, isoprene (2-methyl-1,3-butadiene), *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, Flavivirus (for example deer tick, dengue fever, Powassan, West Nile, yellow fever, or Zika virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. The analyte can be naturally present in the biological fluid, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon, ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA), and intermediaries in the Citric Acid Cycle.

Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g., an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; (2) a mobile phone via auditory and/or visual methods, such as, text message to the host and/or care provider, voice message to the host and/or care provider, and/or 911); (3) a tablet; (4) a smart watch or bracelet; and/or (5) smart glasses or other wearable display device.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. This may be referred to in some cases as two-way authentication.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device (which may also be referred to as an analyte display device), a mobile phone, a tablet, a smart watch, a reference analyte monitor, a drug delivery device, a medical device and a personal computer) may be configured to wirelessly communicate with the sensor electronics module. The plurality of display devices may be configured to display at least some of the displayable sensor information wirelessly communicated from the sensor electronics module. The displayable sensor information may include sensor data, such as raw data and/or transformed sensor data, such as analyte concentration values, rate of change information, trend information, alert information, sensor diagnostic information and/or calibration information, for example.

Analyte Sensor

With reference to FIG. 1A, in some embodiments, analyte sensor 10 includes a continuous analyte sensor, for example, a subcutaneous, transdermal (e.g., transcutaneous), or intravascular device. In some embodiments, such a sensor or device can analyze a plurality of intermittent blood samples. While the present disclosure includes embodiments of glucose sensors, such embodiments may be used for other analytes as well. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the well-being of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 6,001,067 and U.S. Patent Publication No. US-2005-0027463-A1. In some embodiments, analyte sensor 10 is a transcutaneous glucose sensor, such as described with reference to U.S. Patent Publication No. US-2006-0020187-A1. In some embodiments, analyte sensor 10 is configured to be implanted in a host vessel or extracorporeally, such as is described in U.S. Patent Publication No. 2007/0027385A1, co-pending U.S. Patent Publication No. 2008/0119703A1 filed Oct. 4, 2006, U.S. Patent Publication No. 2008/0108942A1 filed on Mar. 26, 2007, and U.S. Patent Application No. 2007/0197890A1 filed on Feb. 14, 2007. In some embodiments, the continuous glucose sensor includes a transcutaneous sensor such as described in U.S. Pat. No. 6,565,509 to Say et al., for example. In some embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In some embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 2A:
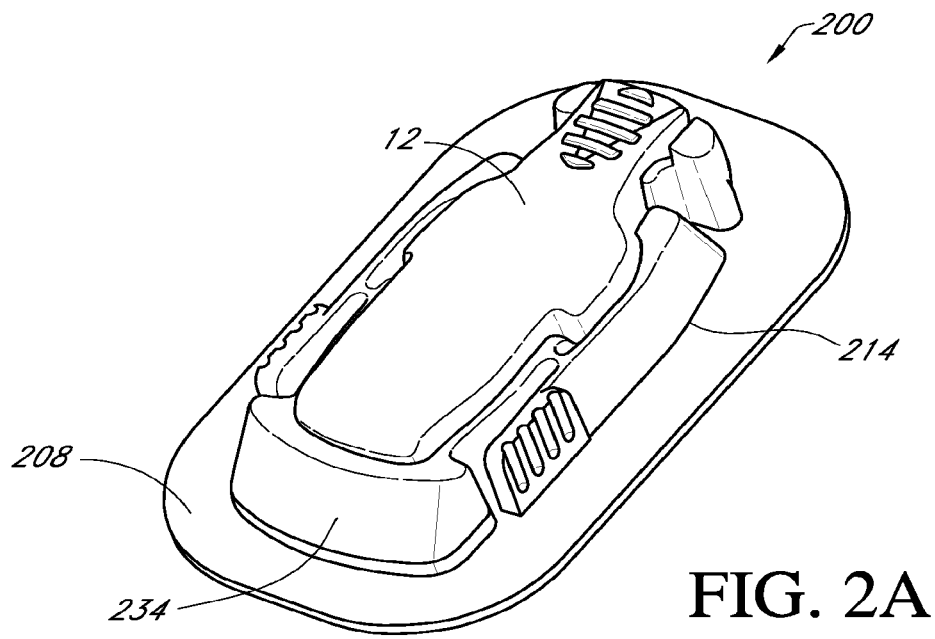
FIG. 2A is a perspective view of an example enclosure that may be used in connection with implementing embodiments of an analyte sensor system.
Figure 2B:
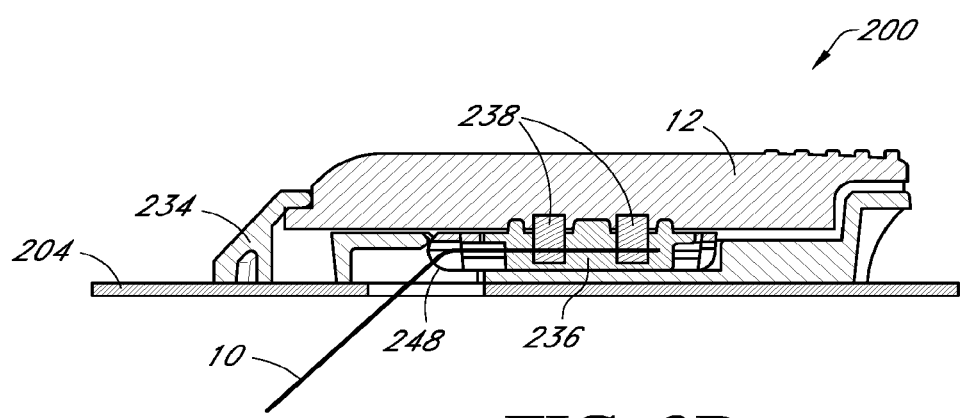
FIG. 2B is a side view of an example enclosure that may be used in connection with implementing embodiments of an analyte sensor system.

FIGS. 2A and 2B are perspective and side views of enclosure 200 that may be used in connection with implementing some embodiments of analyte sensor system 8, according to certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In some embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A and 2B, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. 2009/0240120A1, which is incorporated herein by reference in its entirety for all purposes.

Example Configurations

Referring again to FIG. 1A, system 100 that may be used in connection with implementing aspects of an analyte sensor system is depicted. In some cases, system 100 may be used to implement various systems described herein. System 100 in some embodiments includes analyte sensor system 8 and display devices 110, 120, 130, and 140, according to certain aspects of the present disclosure. Analyte sensor system 8 in the illustrated embodiment includes sensor electronics module 12 and continuous analyte sensor 10 associated with the sensor electronics module 12. Sensor electronics module 12 may be in wireless communication (e.g., directly or indirectly) with one or more of display devices 110, 120, 130, and 140. In some embodiments, system 100 also includes medical device 136 and server system 134. Sensor electronics module 12 may also be in wireless communication (e.g., directly or indirectly) with medical device 136 and server system 134. In some examples, display devices 110-140 may also be in wireless communication with the server system 134 and/or the medical device 136.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can include a display such as a touchscreen display 112, 122, 132, /or 142 for displaying sensor information and/or analyte data to a user and/or receiving inputs from the user. For example, a graphical user interface may be presented to the user for such purposes. In some embodiments, the display devices may include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
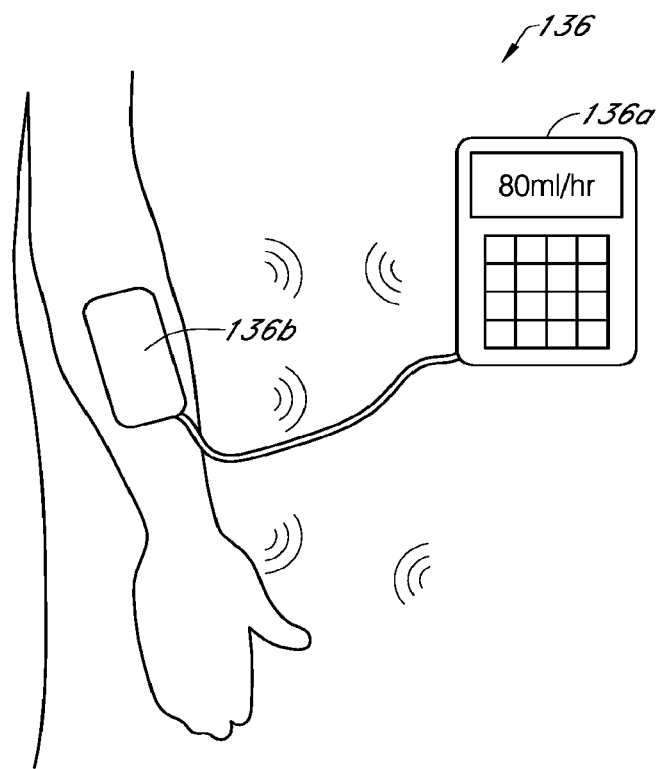
FIG. 1B illustrates aspects of an example system that may be used in connection with implementing embodiments of the disclosure.

Medical device 136 may be a passive device in some example embodiments of the disclosure. For example medical device 136 may be an insulin pump for administering insulin to a user, as shown in FIG. 1B. For a variety of reasons, it may be desirable for such an insulin pump to receive and track glucose values transmitted from analyte sensor system 8. One reason is to provide the insulin pump a capability to suspend or activate insulin administration when a glucose value falls below a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. In some embodiments, the medical device 136 includes a sensor apparatus 136b, e.g., attachable or wearable by the user, in wired or wireless communication with a dedicated monitor or display apparatus 136a to process sensor data and/or display data from the sensor apparatus 136a and/or receive input for operation of the sensor apparatus and/or data processing.

With further reference to FIG. 1A, the plurality of display devices may include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in some implementations of the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 may also include wireless access point (WAP) 138 that may be used to couple one or more of analyte sensor system 8, the plurality display devices, server system 134, and medical device 136 to one another. For example, WAP 138 may provide Wi-Fi and/or cellular connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, and so on.

Figure 3A:
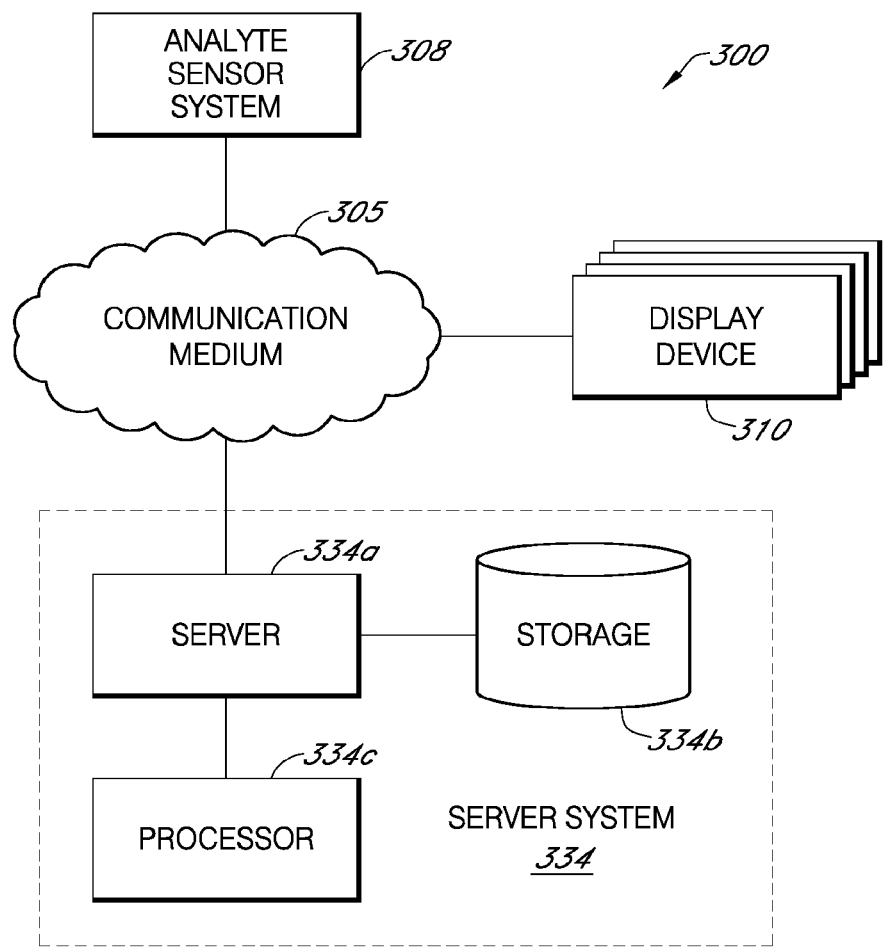
FIG. 3A illustrates aspects of an example system that may be used in connection with implementing embodiments of the disclosure.

Referring now to FIG. 3A, system 300 is depicted. System 300 may be used in connection with implementing embodiments of the disclosed systems, methods, and devices. By way of example, the various below-described components of FIG. 3A may be used to provide wireless communication of glucose data, for example between an analyte sensor system and a plurality of display devices, medical devices, servers and so on, such as those shown in FIG. 1A.

As shown in FIG. 3A, system 300 may include analyte sensor system 308 and one or more display devices 310. Additionally, in the illustrated embodiment, system 300 includes server system 334, which in turn includes server 334a coupled to processor 334c and storage 334b. Analyte sensor system 308 may be coupled to display devices 310 and/or server system 334 via communication medium 305.

As will be described in detail herein, analyte sensor system 308 and display devices 310 may exchange messaging via communication medium 305, and communication medium 305 may also be used to deliver analyte data to display devices 310 and/or server system 334. As alluded to above, display devices 310 may include a variety of electronic computing devices, such as, for example, a smartphone, tablet, laptop, wearable device, etc. Display devices 310 may also include analyte display device 110 and medical device 136. Here, it will be noted that a GUI of display device 310 may perform such functions as accepting user input and displaying menus as well as information derived from analyte data. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 may be based on one or more wireless communication protocols such as Bluetooth, Bluetooth Low Energy (BLE), ZigBee, Wi-Fi, 802.11 protocols, Infrared (IR), Radio Frequency (RF), 2G, 3G, 4G, etc., and/or wired protocols and media.

In various embodiments, the elements of system 300 may be used to perform various processes described herein and/or may be used to execute various operations described herein with regard to one or more disclosed systems and methods. Upon studying the present disclosure, one of skill in the art will appreciate that system 300 may include multiple analyte sensor systems, communication media 305, and/or server systems 334.

As mentioned, communication medium 305 may be used to connect or communicatively couple analyte sensor system 308, display devices 310, and/or server system 334 to one another or to a network, and communication medium 305 may be implemented in a variety of forms. For example, communication medium 305 may include an Internet connection, such as a local area network (LAN), a wide area network (WAN), a fiber optic network, internet over power lines, a hard-wired connection (e.g., a bus), and the like, or any other kind of network connection. Communication medium 305 may be implemented using any combination of routers, cables, modems, switches, fiber optics, wires, radio (e.g., microwave/RF links), and the like. Further, communication medium 305 may be implemented using various wireless standards, such as Bluetooth®, BLE, Wi-Fi, 3GPP standards (e.g., 2G GSM/GPRS/EDGE, 3G UMTS/CDMA2000, or 4G LTE/LTE-U), etc. Upon reading the present disclosure, one of skill in the art will recognize other ways to implement communication medium 305 for communications purposes.

Server 334a may receive, collect, or monitor information, including analyte data and related information, from analyte sensor system 308 and/or display device 310, such as input responsive to the analyte data or input received in connection with an analyte monitoring application running on analyte sensor system or display device 310. In such cases, server 334a may be configured to receive such information via communication medium 305. This information may be stored in storage 334b and may be processed by processor 334c. For example, processor 334c may include an analytics engine capable of performing analytics on information that server 334a has collected, received, etc. via communication medium 305. In some embodiments, server 334a, storage 334b, and/or processor 334c may be implemented as a distributed computing network, such as a Hadoop® network, or as a relational database or the like.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In some embodiments, server 334a at least partially directs communications made over communication medium 305. Such communications include the delivery and/or messaging (e.g., advertisement, command, or other messaging) and analyte data. For example, server 334a may process and exchange messages between analyte sensor system 308 and display devices 310 related to frequency bands, timing of transmissions, security, alarms, and so on. Server 334a may update information stored on analyte sensor system 308 and/or display devices 310, for example, by delivering applications thereto. Server 334a may send/receive information to/from analyte sensor system 308 and/or display devices 310 in real time or sporadically. Further, server 334a may implement cloud computing capabilities for analyte sensor system 308 and/or display devices 310.

Figure 3B:
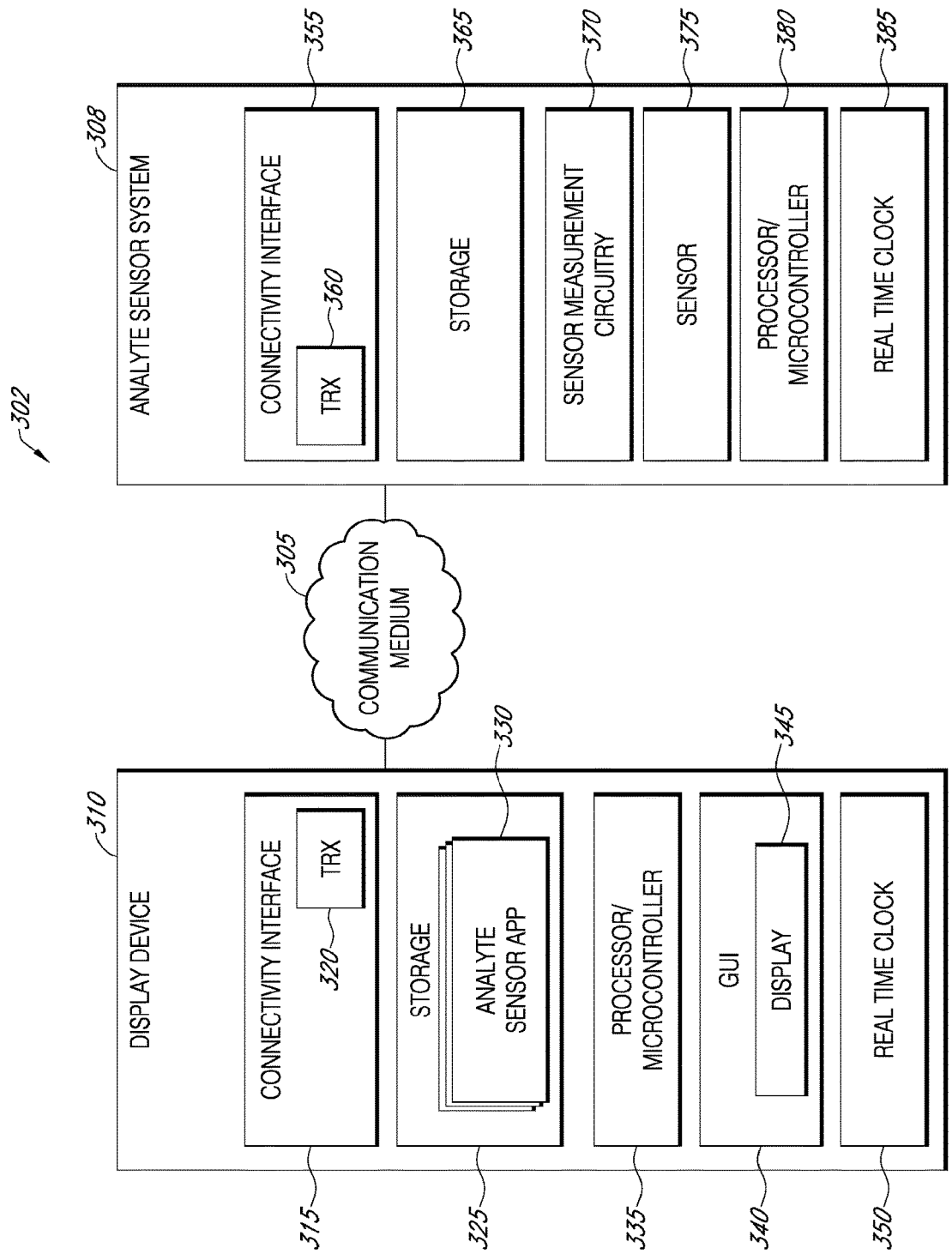
FIG. 3B illustrates aspects of an example system that may be used in connection with implementing embodiments of the disclosure.

FIG. 3B depicts system 302, which includes examples of additional aspects of the present disclosure that may be used in connection implementing an analyte sensor system. As illustrated, system 302 may include analyte sensor system 308. As shown, analyte sensor system 308 may include analyte sensor 375 (e.g., which may also be designated with the numeral 10 in FIG. 1A) coupled to sensor measurement circuitry 370 for processing and managing sensor data. Sensor measurement circuitry 370 may be coupled to processor/microprocessor 380 (e.g., which may be part of item 12 in FIG. 1A). In some embodiments, processor 380 may perform part or all of the functions of the sensor measurement circuitry 370 for obtaining and processing sensor measurement values from sensor 375. Processor 380 may be further coupled to a radio unit or transceiver 320 (e.g., which may be part of item 12 in FIG. 1A) for sending sensor data and receiving requests and commands from an external device, such as display device 310, which may be used to display or otherwise provide the sensor data (or analyte data) to a user. As used herein, the terms "radio unit" and "transceiver" are used interchangeably and generally refer to a device that can wirelessly transmit and receive data. Analyte sensor system 308 may further include storage 365 (e.g., which may be part of item 12 in FIG. 1A) and real time clock (RTC) 380 (e.g., which may be part of item 12 in FIG. 1A) for storing and tracking sensor data.

As alluded to above, wireless communication protocols may be used to transmit and receive data between analyte sensor system 308 and the display device 310 via communication medium 305. Such wireless protocols may be designed for use in a wireless network that is optimized for periodic and small data transmissions (that may be transmitted at low rates if necessary) to and from multiple devices in a close range (e.g., a personal area network (PAN)). For example, one such protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing overhead) to reduce power consumption. In some embodiments, burst broadcasting schemes (e.g., one way communication) may be used. This may eliminate overhead required for acknowledgement signals and allow for periodic transmissions that consume little power.

The protocols may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as Wi-Fi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

With further reference to FIG. 3B, system 302 may include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335, graphical user interface (GUI) 340 that may be presented using display 345 of display device 310, and real time clock (RTC) 350. A bus (not shown here) may be used to interconnect the various elements of display device 310 and transfer data between these elements.

Display device 310 may be used for alerting and providing sensor information or analyte data to a user, and may include a processor/microprocessor 335 for processing and managing sensor data. Display device 310 may include display 345, storage 325, analyte sensor application 330, and real time clock 350 for displaying, storing, and tracking sensor data. Display device 310 may further include a radio unit or transceiver 320 coupled to other elements of display device 310 via connectivity interface 315 and/or a bus. Transceiver 320 may be used for receiving sensor data and for sending requests, instructions, and/or data to analyte sensor system 308. Transceiver 320 may further employ a communication protocol. Storage 325 may also be used for storing an operating system for display device 310 and/or a custom (e.g., proprietary) application designed for wireless data communication between a transceiver and display device 310. Storage 325 may be a single memory device or multiple memory devices and may be a volatile or non-volatile memory for storing data and/or instructions for software programs and applications. The instructions may be executed by processor 335 to control and manage transceiver 320.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver 320, 360.

Components of analyte sensor system 308 may require replacement periodically. For example, analyte sensor system 308 may include an implantable sensor 375 that may be attached to a sensor electronics module that includes sensor measurement circuitry 370, processor 380, storage 365, and transceiver 360, and a battery (not shown). Sensor 375 may require periodic replacement (e.g., every 7 to 30 days). The sensor electronics module may be configured to be powered and active for much longer than sensor 375 (e.g., for three to six months or more) until the battery needs replacement. Replacing these components may be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it may be connected to sensor 375 and a sensor session may be established. As will be further described below, there may be a process for initially establishing communication between display device 310 and the sensor electronics module when the module is first used or re-activated (e.g., the battery is replaced). Once display device 310 and sensor electronics module have established communication, display device 310 and the sensor electronics module may periodically and/or continuously be in communication over the life of several sensors 375 until, for example, the battery needs to be replaced. Each time sensor 375 is replaced, a new sensor session may be established. The new sensor session may be initiated through a process completed using display device 310 and the process may be triggered by notifications of a new sensor via the communication between the sensor electronics module and display device 310 that may be persistent across sensor sessions.

Analyte sensor system 308 typically gathers analyte data from sensor 375 and transmits the same to display device 310. Data points regarding analyte values may be gathered and transmitted over the life of sensor 375 (e.g., in the range of 1 to 30 days or more). New measurements may be transmitted often enough to adequately monitor glucose levels. Rather than having the transmission and receiving circuitry of each of analyte sensor system 308 and display device 310 continuously communicating, analyte sensor system 308 and display device 310 may regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 may be communicatively coupled to analyte sensor system 308 via communication medium 305. Transceiver 320 of connectivity interface 315 may include multiple transceiver modules operable on different wireless standards. Transceiver 320 may be used to receive analyte data and associated commands and messages from analyte sensor system 308. Additionally, connectivity interface 315 may in some cases include additional components for controlling radio and/or wired connections, such as baseband and/or Ethernet modems, audio/video codecs, and so on.

Storage 325 may include volatile memory (e.g., RAM) and/or non-volatile memory (e.g., flash storage), may include any of EPROM, EEPROM, cache, or may include some combination/variation thereof. In various embodiments, storage 325 may store user input data and/or other data collected by display device 310 (e.g., input from other users gathered via analyte sensor application 330). Storage 325 may also be used to store volumes of analyte data received from analyte sensor system 308 for later retrieval and use, e.g., for determining trends and triggering alerts. Additionally, storage 325 may store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user may interact with analyte sensor application 330 via GUI 340, which may be provided by display 345 of display device 310. By way of example, display 345 may be a touchscreen display that accepts various hand gestures as inputs. Application 330 may process and/or present analyte-related data received by display device 310, according to various operations described herein, and present such data via display 345. Additionally, application 330 may be used to obtain, access, display, control, and/or interface with analyte data and related messaging and processes associated with analyte sensor system 308, as is described in further detail herein.

Application 330 may be downloaded, installed, and initially configured/setup on display device 310. For example, display device 310 may obtain application 330 from server system 334, or from another source accessed via a communication medium (e.g., communication medium 305), such as an application store or the like. Following installation and setup, application 330 may be used to access and/or interface with analyte data (e.g., whether stored on server system 334, locally from storage 325, or from analyte sensor system 308). By way of illustration, application 330 may present a menu that includes various controls or commands that may be executed in connection with the operating of analyte sensor system 308 and one or more display devices 310. Application 330 may also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. In some implementations, application 330 may interact with other application(s) of the display device to retrieve or provide relevant data, e.g., such as other health data.

Analyte sensor application 330 may include various code/functional modules, such as, for example, a display module, a menu module, a list module, and so on as will become clear in light of the description of various functionalities herein (e.g., in connection with disclosed methods). These modules may be implemented separately or in combination. Each module may include computer-readable media and have computer-executable code stored thereon, such that the code may be operatively coupled to and/or executed by processor 335 (which, e.g., may include a circuitry for such execution) to perform specific functions (e.g., as described herein with regard to various operations and flow charts etc.) with respect to interfacing with analyte data and performing tasks related thereto. As will be further described below, a display module may present (e.g., via display 345) various screens to a user, with the screens containing graphical representations of information provided by application 330. In further embodiments, application 330 may be used to display to the user an environment for viewing and interacting with various display devices that may be connectable to analyte sensor system 308, as well as with analyte sensor system 308 itself. Sensor application 330 may include a native application modified with a software design kit (e.g., depending on the operating system) in order to carry out the functionalities/features described herein.

Referring again to FIG. 3B, display device 310 also includes processor 335. Processor 335 may include processor sub-modules, including, by way of example, an applications processor that interfaces with and/or controls other elements of display device 310 (e.g., connectivity interface 315, application 330, GUI 340, display 345, RTC 350, etc.). Processor 335 may include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller may include various controls related to the gathering of user input, such as, for example, a user's finger print (e.g., to authorize the user's access to data or to be used for authorization/encryption of data, including analyte data), as well as analyte data.

Processor 335 may include circuitry such as logic circuits, memory, a battery and power circuitry, and other circuitry drivers for periphery components and audio components. Processor 335 and any sub-processors thereof may include logic circuits for receiving, processing, and/or storing data received and/or input to display device 310, and data to be transmitted or delivered by display device 310. Processor 335 may be coupled by a bus to display 345 as well as connectivity interface 315 and storage 325 (including application 330). Hence, processor 335 may receive and process electrical signals generated by these respective elements and thus perform various functions. By way of example, processor 335 may access stored content from storage 325 at the direction of application 330, and process the stored content for display and/or output by display 345. Additionally, processor 335 may process the stored content for transmission via connectivity interface 315 and communication medium 305 to other display devices 310, analyte sensor system 308, or server system 334. Display device 310 may include other peripheral components not shown in detail in FIG. 3B.

In further embodiments, processor 335 may further obtain, detect, calculate, and/or store data input by a user via display 345 or GUI 340, or data received from analyte sensor system 308 (e.g., analyte sensor data or related messaging), over a period of time. Processor 335 may use this input to gauge the user's physical and/or mental response to the data and/or other factors (e.g., time of day, location, etc.). In various embodiments, the user's response or other factors may indicate preferences with respect to the use of certain display devices 310 under certain conditions, and/or the use of certain connection/transmission schemes under various conditions, as will be described in further detail herein.

It should be noted at this juncture that like-named elements as between display device 310 and analyte sensor system 308 may include similar features, structures, and/or capabilities. Therefore, with respect to such elements, the description of display device 310 above may in some cases be applied to analyte sensor system 308.

Technical Support

Continuous analyte monitors have been increasing in popularity as both a convenient and necessary way to monitor and always be aware of a user's analyte levels. As a result, the user base utilizing the above-described analyte monitoring system continues to expand, as has the volume of calls to a patient support hotline, accordingly. A typical call to a patient support center entails several aspects. For example, a tech support technician typically spends 10-45 minutes on the phone diagnosing and resolving an issue for which a patient has placed a patient support call. In the context of a medical device, patient support calls trigger several behind the scene obligations unique to such environment, which differ from a typical support call in the context of consumer goods not regulated by a regulatory body, such as the U.S. Food and Drug Administration (FDA). The regulatory context, within which a medical device provider operates, may create an obligation on the provider to record or report calls made to its patient support center related to the medical devices sold by the provider. In such context, the conventional technical support staff, in addition to resolving patient issues, may have to spend considerable amount of time complying with or fulfilling the medical device provider's regulatory obligations. Additionally, several departments within a medical device provider organization may wish to interface with the technical support center to identify trending issues in existing products, or to determine patients' desired features or in general needed improvements in the devices of the medical device provider. Consequently, the need for quality assurance, product tracking or general improvements creates a separate reporting obligation for the staff of a patient support center. With increases in patient base, the conventional methods of handling patient reported issues or questions become impractical or difficult to implement. The disclosed systems and methods can provide automated or semi-automated technical support and associated logging, recording and regulatory compliance as may be appropriate for a medical device provider.

Example Embodiments of Technical Support Systems/Methods

The embodiments described herein can comprise situations when the described systems or methods proactively, or as a result of an initiating request for tech support from a patient, automatically or semi-automatically identify, resolve technical issues, provide one or more appropriate notifications to affected patients, patients' remote monitors or third parties and record the tech support issues, resolutions and associated data in appropriate databases, including regulatory compliance databases.

FIG. 4 illustrates an example architecture of an automated or semi-automated technical support system in accordance with embodiments of the present technology. A continuous analyte sensor 402, such as a continuous glucose sensor referred to as CGM 402, for example, can be inserted in a patient (e.g., transcutaneously) to sense and transmit medical data (e.g., glucose analyte data) of a patient to one or more transceivers 404a and 404b. As described above, the transceivers 404a and 404b can be custom analyte monitoring display devices or computing devices such as smart phones, tablets, smart glasses, smart watches, desktop computers or a combination of these or similar devices. In the disclosure herein, the terms "transceiver" and "receiver" may be used interchangeably to refer to components similar to the transceivers 404a and 404b. Examples of the CGM 402 can include analyte sensor system 8, and examples of transceivers 404a and 404 can include the sensor electronics module 12 of analyte sensor system 8 or any of the display devices 110, 120, 130 and 140 as shown in FIG. 1A, and/or the like. The CGM 402 may produce multiple streams of data and selectively route the data streams to the transceivers 404a and 404b. In the example shown in FIG. 4, the CGM 402 can produce real time data. Real time data can include one or more of estimated glucose value(s) (EGV), glucose concentration rate of change information, CGM alert information, raw sensor data, and/or other type of public or private data. Real time data is separated from bulk data because action may need to be taken based on the real time data in an immediate or timely manner.

Generally, public data includes information that is presented to a patient in charts or reports such as glucose values, monitor/calibration values, time adjustments, event entries by a patient (like meals, carbs, exercise, etc.), when sensors were started/stopped, which transmitter was used and when, and the like. While private data generally comprises information about the system and devices that comprise the system such as battery levels, screen durations, error logs, raw sensor signals, proprietary algorithm input/output, stack dumps of memory, and the like.

Public data and private data can comprise one or both of real time data and bulk data. Bulk data can include, for example, data points such as system software version information, diagnostic information, other proprietary data and stored readings such as glucose levels recorded over a time period such as one hour, two hours, etc. While real time data can include, for example, data points such as monitored glucose levels, timestamps associated with monitored values, glucose monitor status, and the like. Generally, real time data is data that is transmitted by the CGM 402 or transceivers 404a, 404b as it is created or shortly thereafter (e.g., intermittently or periodically, such as every one minute, five minutes, 10 minutes, etc.), while bulk data is data that may be stored on the CGM 402 or the transceivers 404a, 404b for a longer period of time than real time data (e.g., one hour) and transmitted less frequently than real time data.

The transceivers 404a and 404b can in turn transmit their respective data to a cloud computing architecture 410. The cloud computing architecture 410 can include a real time server 408 for receiving and processing real time data from the transceiver 404a. The cloud computing architecture 410 can also include a bulk data collector (BDC) 412 for receiving and processing bulk data from the transceivers 404a and 404b. The real time data can be shared with a remote monitor 416 operated by a caregiver user, e.g., affiliated with the patient user. For example, in some cases, a patient's parent or guardian can have access to the remote monitor 416 for the purpose of remotely monitoring the patient's health and receiving system alarms related to patient's health. Examples of systems and methods for remote monitoring of analyte data, such as by remote monitor 416, are described in more detail in U.S. Patent Publication Nos. 2014/0184422 and 2014/0187889, all of which are incorporated herein by reference in their entirety for all purposes.

In some embodiments, the cloud computing architecture 410 includes a tech support server 422. The tech support server 422 can include one or more computers (e.g., servers) in communication with one or more databases to form a tech support system 420 for diagnosing and resolving patients' technical issues associated with a medical device, such as CGM 402 and/or transceiver 404a, 404b, and handling subsequent logging and reporting associated with those technical issues. Various embodiments of the tech support system 420 are described that comprise the tech support server 422 in communications with a patient records server or database 424, product records server or database 426, an accounting server or database 428, a regulatory records server or database 430, and/or a tech issues & solutions server or database 432.

In some embodiments, the cloud computing architecture 410 further includes bulk data distributor (BDD) 414. The BDD 414 can provide a portion of the data in the BDC 412 to the tech support server 422. In some embodiments, the tech support server 422 can be in direct communication with one or more of transceivers 404a and 404b.

In some embodiments of the tech support system 420, the tech support server 422 can communicate with a patient records database 424. In some cases, for example, diagnosing or resolving a patient's complaint involves an investigation or query of the patient's records. Such investigation can reveal information relevant to resolving the patient's technical issue. For example, the investigation can help determine what sensor the patient is currently using, the age of the sensor, or other historical data related to the patient's hardware, software or the patient's prior technical issues. In some instances, the automated or semi-automated systems and methods described herein can automatically order replacement parts, for example replacement sensors, and automatically update the appropriate patient's records in the patient records database 424.

In some embodiments of the tech support system 420, the tech support server 422 can communicate with a product records server 426. Technical issues discovered automatically, or as a result of a patient's communication with the tech support server 422, can contain information relevant to product development, quality assurance and general future improvements of features of the devices of the medical device provider. In some implementations, the tech support server 422 can communicate with the product records server 426 for tracking technical issues associated with the hardware provided by the medical device provider. Such product tracking may help to trace the cause of an issue to a particular batch of products coming from a particular laboratory or manufacturing lot. The tech support server 422 or the product records server 426 can use this information to trigger remedial measures aimed at resolving similar issues before patients have to place a request for service or initiate a tech support ticket. In instances where the described systems and methods proactively resolve an issue, without any initiating action of the patient, a notification can be issued to the affected patients alerting them to the existence of the issue and the subsequent resolution undertaken automatically by the system.

In some embodiments of the tech support system 420, the tech support server 422 can be configured to both store and query a tech issues & solutions database 432. The database 432 can be a knowledge database updated automatically by the tech support server 422 or by the tech support personnel operating a tech support personnel computing system 434. Some references to the tech support personnel computing system 434 may refer to the personnel operating the computing system 434. The tech issues & solutions database 432 can maintain histories and logs of issues the patients have experienced as well as known solutions to those issues. In some embodiments, data or population analytics can be run on the data in the database 432 or alternatively on data provided by the BDD 414. Tech support reports of varying duration (e.g., top 10 or top 5 reported issues since last week, last month, last three months, etc.) can be generated from the data in the tech issues & solutions database 432 to improve the products or services provided. For example, a top ten issues list over the past month can be compiled and presented (e.g., via an automated email) to the medical device provider's engineers. Issues can be ranked based on the time period in which they occurred, their frequency and their severity. The ability to generate system-wide issue reports enables identifying and distinguishing between unimportant or infrequent patient technical issues versus emerging trends in issues that affect many patients and their respective analyte monitoring systems. In some embodiments, issues and errors encountered by the patients may be assigned a numerical key that can facilitate running data analytics and reporting as described above.

For example, by addressing a limited quantity of top-ranked tech support issues using methods and systems in accordance with the present technology (e.g., such as the top 6 issues related to the software application based on user interaction, user education, improved UI/UX, and/or other forms of 'soft' improvements), the call volume to the tech support center (e.g., tech support personnel 434) can be reduced substantially, e.g., such as up to 50% reduction of the example top 6 issues. Also, for example, addressing the top-ranked issues may improve saving flows to the other downstream activities that tech support issues subsequently cause (e.g., such as QA/Regulatory etc., as well as may improve customer retention. Examples of the top-ranked tech support issues can include a question mark icon ("???") presented in the status box (e.g., associated with communication disruptions between transmitter and receiver), inaccurate calibrations, hardware error icons, or others.

Such automated coding of errors can improve the patient's experience when troubleshooting an issue. In some cases, when addressing a technical issue through conventional channels of patient support, patients do not refer to various components of the analyte monitoring system by correct terminology. Consequently, time and resources are spent attempting to identify the technical issue for which a patient is contacting tech support. For example, when discussing a technical issue with tech support technician, a patient may incorrectly state that his sensor does not work, while the issue may be that the patient's receiver does not turn on. Consequently, the technician attempts to resolve the issue by applying sensor failure troubleshooting scripts. In some cases, the technician may incorrectly order replacement sensors for the patient, while the issue may reside in the patient's receiver. In examples where the patient's receiver is a mobile computing device such as smart phone 120 and the like, which has analyte sensor application 330 operating thereon, when the analyte sensor application 330 automatically categorizes and associates an error code to an error message according to the embodiments described herein, it will query various components and status of the medical device and can correctly identify the parts which may be experiencing issues. Consequently, an error ticket can be generated correctly identifying parts that may need troubleshooting.

In some embodiments, the patient can encounter an alert or error message on the transceivers 404a and/or 404b, e.g., which can be embodied as display devices 110-140 as in FIG. 1A and referred to as display device(s) 404. An error code can be associated with the alert or the error message which the patient is viewing on his display device. In some embodiments, the patient can add information to the error message about the context in which the error message was received and transmit the augmented error message to the tech support server 422. In some embodiments, the display device 404 can augment the error message with additional information that may assist the technical server 422 in resolving the technical issue. Examples of context information the patient can add to the error message can include whether the patient had just engaged in strenuous exercise activity, had taken a meal or administered insulin. Examples of information which can be added by the display device 404 can include the operating system, the hardware and its version, other concurrently running applications (if appropriate patient permissions have been obtained). In some embodiments, appropriate patient permissions related to HIPAA and/or other legal or regulatory privacy issues can be obtained and appended to the error message and subsequently transmitted to the tech support server 422. As described, an error code can be associated with the error message and transmitted along with the necessary permissions and patient contact information to the tech support server 422, as part of an error ticket. The operations associated with building an error ticket can be handled by the analyte sensor application 330 running on the display devices 404.

The error ticket can be transmitted to the tech support system 420 via a wired or wireless communication, for example, via the communication medium 305 as described above. In some embodiments, the tech support server 422 receives the error ticket. The tech support server 422 can include software modules to automatically or semi-automatically record the incident described in the error ticket in one or more relevant databases of the medical device provider. For example, the tech support server can record the incident contained in the error ticket in the relevant patient record in the patient records 424, in product records 426, in regulatory records 430 and/or the tech issues & solutions 432. The tech support server 422 can diagnose the issue associated with the incident reported in the error ticket locally or via communication with the tech support personnel 434. In some embodiments, the tech support server 422 can query the tech issues & solutions database 432 to resolve the issues identified in the error ticket. The tech support server 422 can take remedial measures automatically or semi automatically in response to the incident reported in the error ticket. For example, the tech support server 422 can initiate ordering a sensor replacement as will be described further below. In some embodiments, the tech support server 422 can send over-the-air (OTA) software updates to the display devices 404 to resolve the issues identified in the error ticket.

In some embodiments, the tech support server 422 can communicate with various databases of a medical device provider within or without the tech support system 420 for various purposes. For example, upon identification and resolution of an issue, the tech support server 422 can further update one or more databases of the medical device provider, for example, patient records 424, product records 426, accounting 428, tech issues & solutions 432, and/or regulatory records 430.

The read or write operations into and out of the various databases of the medical device provider as described herein are meant as examples. Persons of ordinary skill in the art can readily envision a multitude of read and write operations between various databases of the medical device provider for the purposes of diagnosing and resolving patient technical issues, while providing proper record keeping for regulatory, product, accounting or other purposes associated with tech support.

In some embodiments, before an automated execution of a determined resolution, the tech support system 420, by request, automatically, by decision tree, or randomly, can provide the error ticket information and determined resolution to the tech support personnel 434 for the purposes of error identification, verification of solution, or to provide a check on the automated tech support system, for example based on statistically driven methods.

The identification and resolution of a technical issue may not involve an action of the patient. For example, the analyte sensor application 330 running on the display device 404 can detect data gaps between certain hours of night. The analyte sensor application 330 running on the display device 404 can generate an error ticket with an error code which identifies this issue as "data gaps at night," and append contextual data to the error ticket as described herein. In some embodiments, appropriate patient permissions can be obtained prior to detecting an incident and used when an issue is detected and an error ticket is built. If patient permissions have previously been obtained, the analyte sensor application 330 can append those permissions to the error ticket, or if those permissions are not previously obtained, the analyte sensor application 330 can prompt the user for those permissions, append the obtained permissions to the error ticket and transmit the error ticket to the tech support server 422. The tech support server 422 can extract the error code from the error ticket and search the database of known issues in the tech issues & solutions database 432. The error code may have, for example, identified one or more conflicting applications running in the background of the display devices 404, which causes data gaps at nighttime. A message can be generated by the tech support server 422 and transmitted as an alert to the display devices 404 containing a message alerting the patient about the detection of the issue of data gaps at night and the suggested solution of closing those applications during nighttime.

Some technical issues can be resolved at the application level on the display devices 404, without generating or transmitting an error ticket. For example, the monitored analyte values are by design allowed to be outside range for some 10 to 20% of the time during an analyte monitoring session. Some patients may not be aware of such or other system limitations and incorrectly assume that these system limitations amount to technical issues. When there is an attempt to generate an error ticket based on such issues, the analyte sensor application 330 can alert the patient thus alleviating the need to generate or transmit error tickets. In some embodiments, an information button, for example in the form of the uppercase or lowercase letter I (i.e., "i") or other symbol can be displayed along with any alert issued by the analyte sensor application 330. The patient can click on the information button and obtain more information about the displayed alert. For example, an alert indicating "sensor readings cannot be obtained" may be because the system requires more time to process and display sensor readings. When the patient clicks on the information button, a message explaining that "a waiting period is normal before sensor readings can be obtained" may be displayed on the display devices 404. In another example, if an "out of range" symbol is not accompanied by an appropriate text, clicking on the information button can clarify, for example via a text box shown on the display devices 404, that the transceiver may be out of range. In other examples, various timing or durations associated with an alert message or an error message can determine whether or not an error ticket is generated. For example, if an error is detected to have persisted for a duration less than a threshold (e.g., less than an hour), the analyte sensor application 330 may halt generation of an error ticket until that threshold is reached. If the error persists for more than the duration threshold (e.g., an hour), an appropriate error ticket can be generated and transmitted as described herein. The threshold duration can be tied to or based on the underlying alert or error message.

In some embodiments of the tech support system 420, the analyte sensor application 330 can be retrofitted with software modules or algorithms for resolving patient technical issues based on detection of configuration and status of the display devices 404. Resolution of some patient technical issues involves intervention by the tech support personnel 434. For example, in some cases, the display device 404 may be retrofitted with an "airplane mode," such that toggling this mode to "on" position, shuts off all wireless communications of the display device 404. The patient may place a phone call to tech support personnel 434 complaining about the display device 404's inability to capture the analyte data wirelessly. The tech support personnel 434 may have to apply several troubleshooting scripts for resolving the issue before realizing that the patient's display device 404 has the airplane mode in the "on" position. In some embodiments, the analyte sensor application, can locally detect that the display device 404 is in an "airplane mode" and issue an appropriate alert to the patient (automatically or as a result of patient's action to initiate a tech support request). Such issues and subsequent resolution may still be reported to the tech support server 422 and recorded and reflected in the tech issues & solutions database 432 or other databases associated with the tech support system 420 for a variety of purposes, for example for product improvement, or better user interface design.

As described herein, the tech issues & solutions database 432 can interface with engineering & design team computing system 436 for the purpose of providing data on appropriate improvements to the products and services of the medical device provider. Some references to engineering & design team computing system 436 may refer to the engineering & design team personnel operating the computing system 436. When the design or engineering personnel have visibility into tech issues, they can take appropriate action. For example, the user interface designers in collaboration with engineers may incorporate a feature in an update to the analyte sensor application 330 where the "on" status of an "airplane mode" is automatically detected and an alert is automatically issued to the patient explaining that obtaining analyte data via wireless connection is suspended until the "airplane mode" is turned off. Consequently, the systems and methods described herein not only provide automatic or semi-automatic resolution of technical issues, but they provide visibility of the ongoing technical issues to appropriate teams within the medical device provider for efficient and proactive resolution of those issues.

In some embodiments of the tech support system 420, the technical issues and resolutions recorded in the tech issues & solutions database 432 may additionally be encoded with an identifier of the tech support personnel 434. In a given technical support environment, the tech support personnel can develop expertise and skills in various areas. Such specialization can make troubleshooting patient's issues more efficient, increasing patient's satisfaction. By mapping the technical issues to the appropriately skilled personnel, the systems and methods described herein can, when needed, route patient calls to the appropriately skilled personnel within the tech support personnel 434 to efficiently achieve resolution of patient's technical issues. Additionally, members of the engineering & design team 436 can more efficiently reach the appropriately skilled tech support personnel 434 when examining tech support issues reports and attempting to improve products or fix issues.

In some embodiments of the tech support system 420, the solutions embedded in the tech issues & solutions database 432 can be assigned a rating score based on how frequently the solution has been helpful to resolving patient's technical issues. The tech support server 422 can routinely and automatically comb through the solutions embedded in the tech issues & solutions database 432 and purge the database from solutions that have routinely been given a low score.

In some embodiments of the tech support system 420, the tech support server 422 may work in conjunction with the tech support personnel 434 in real time. For example, as a tech support personnel 434 troubleshoots a patient's technical issue, the tech support server 422 can search the tech issues & solutions database 432 for other tech support personnel who may have recent experiences with a similar issue. Subsequently, the tech support server 422 can connect the two tech support personnel via an on-screen chat box or other methods to provide for an ability of the tech support personnel 434 to query and use other tech support personnel's knowledge and skill in resolving patients' technical issues.

In some embodiments of the tech support system 420, the tech support server 422 can categorize an issue and consult an appropriate troubleshooting script in the tech issues & solutions database 432. Alternatively, if the tech support server 422 determines that the resolution of the issue is better left to a tech support personnel 434, the tech support server 422 can route the issue to a tech support personnel 434 who is known to be skilled in handling the issue.

In some embodiments of the tech support system 420, the tech issues & solutions database 434 can contain history of issues associated with previous products of the medical device provider. Running data analytics and comparisons between the current products of the medical device provider and known historical trends of previous products can provide insights on whether a particular technical issue should receive more attention.

In some embodiments of the tech support system 420, the tech support server 422 can be configured with appropriate thresholds to automatically alert when the reports from the tech issues & solutions database 432 surpasses those thresholds. In some embodiments, system-wide reports can be run on data which is not subject to HIPAA. The engineering & design team 436 can subsequently indicate whether a particular issue reported to them was acknowledged and have been added to their workload. Consequently, an analysis of the tech issues & solutions database 432 can reveal issues that have not yet been acknowledged or acted upon by the engineering & design team 436. The ability of the engineering & design team 436, to have visibility into the technical issues encountered by the patients, enables the engineering & design team 436 to proactively experiment with various solutions and potentially update the tech issues & solutions database 432 with new solutions for emerging issues.

In some embodiments of the tech support system 420, the tech support server 422 can further communicate with an accounting server 428. In some cases, resolving a patient's technical issue can entail modifications to the medical device provider's one or more accounting databases. For example, the automated methods and systems described herein can determine that a resolution of a patient's technical issue entails ordering of a sensor replacement. The system can therefore order a replacement sensor to be shipped to the patient. The system can subsequently create an invoice for the patient. Alternatively, if the sensor replacement is to be provided free of charge the tech support server 422 in association with the accounting server 428, can record this event in appropriate company accounting databases as a tax-deductible eligible event.

In some embodiments of the tech support system 420, the tech support server 422 can proactively search for and detect technical issues by running population data analytics (e.g., based on multiple patient experiences) on the bulk data contained in the BDC 412 or data provided by the BDD 414. Conventionally, technical issues would have to be reported and logged through regular technical support channels. Months of patients' calls need to be manually analyzed before trends in the emerging or potential issues could be detected. However, by proactively mining the data in the BDC 412 and/or BDD 414, emerging trends and potential issues can be detected and remedied before they can afflict many patients. In some embodiments, remedying detected technical issues include tech support system 420 sending over-the-air (OTA) software fixes to display devices 404.

The real time data stored on the real time server 408 and the bulk data stored on the BDC 412 can be analyzed, separately or together, for the purposes of providing proactive tech support. Such analysis can reveal latent or overt technical issues. In some embodiments of the tech support system 420, the tech support server 422 can compare different streams of data associated with same reading sessions to detect discrepancies indicative of an underlying technical issue. In some embodiments, the data stored on the real time server 408 and the BDC 412 can contain duplicative analyte data associated with same analyte read out sessions. Discrepancies between the streams of data stored in different databases can indicate the existence of a technical issue. In some embodiments, for example, algorithms comparing the data streams stored in the real time server 408 and the BDC 412 can detect discrepancies and determine that the discrepancies indicate a calibration error. The tech support server 422 can generate a message on the display device 404 alerting the patient to recalibrate.

In some embodiments of the tech support system 420, the tech support server 422 can be configured to analyze the data on one or more reading sessions stored on the real time server 408 or BDC 412 in order to diagnose and resolve an error ticket initiated by the user or the analyte sensor application 330.

Tech Support Via Remote Monitoring

In some embodiments of the tech support system 420, the tech support server 422 can be configured to be in communication with the remote monitor 416. In some instances, the remote monitor 416 may desire to initiate an error ticket. For example, the remote monitor 416 may not receive analyte data and/or alerts, via the real time server 408, associated with the patient user's analyte state monitored by CGM 402 and transceiver 404A, 404B. In such cases, in some implementations, the remote monitor 416 can initiate an error ticket similar to the way a transceiver 404A generates and transmits an error ticket as described herein. The remote monitor 416 can add authentication or verification data in the error ticket to identify itself as a HIPAA authorized user. In case of a loss of reading, the tech support server 422 may recall and execute an appropriate troubleshooting script. For example, the tech support server 422 can query the status of the transceiver 404A to determine whether the transceiver 404A is receiving analyte readings. If, for example, the transceiver 404A transmits a status "out of range" to the tech support server 422, a message explaining this status can be conveyed to the remote monitor 416, alerting the remote monitor that the patient's transceiver is out of range.

In some embodiments, the remote monitor 416 receives real time data from the real time server 408. An error ticket and a request for tech support generated by the remote monitor 416 can include real time data. In some embodiments of the tech support system 420, the tech support server 422 can be configured to analyze real time data contained in an error ticket from a remote monitor 416 in conjunction with the bulk data from the BDD 414 to diagnose and resolve the error ticket using techniques described herein. The tech support server 422 can be in communication with an authentication system to authenticate the remote monitor 416 prior to communicating with the remote monitor 416.

In some embodiments, the remote monitor 416 is presented with real time data in a visual form or graphical display. A remote monitor 416 can detect and initiate an error ticket based on inspection of the visual or graphical display. The tech support system 420 may also have access to same or similar copies of the visual or graphical displays transmitted to the remote monitor 416, and can decode an error ticket generated based on the visual or graphical displays. The tech support system 420 can include visual or graphical display data including, data tables, charts, data categories (e.g., estimated glucose values (EGVs), logs, etc.) with the same or similar visual or graphical display data as provided to the remote monitor 416. In some embodiments, the visual or graphical display data can include charts presenting data in a chronological form. In some embodiments, the visual or graphical display data can include an identification of the source of the data (e.g., hardware or software generating or initiating the visual or graphical display).

In some embodiments, the tech support system 430 may include one or more tools for automatically or semi-automatically downloading relevant data from and analyzing one or multiple returned display devices 404 or returned CGM devices 402. In conventional customer support environments, the cost and administrative burden of properly analyzing a returned unit may be prohibitive. Consequently, product improvements or troubleshooting advantages, which could be gained from analyzing such returned units, may be forfeited. In some embodiments, the tech support system 420, can request that a patient return a custom analyte display device or a CGM 402 for further troubleshooting and analysis. The patient can be provided with shipment material for returning these items. The tech support system 420 can utilize a variety of tools to download and analyze the relevant data embedded on returned devices both for troubleshooting and assisting the patient who returned the items, as well as collecting technical data for a multitude of returned units from multiple patients to identify, alert or resolve issues affecting multiple devices. In some embodiments, the tech support system 420 includes a repository tool for downloading and analyzing analyte data from a custom analyte display device. In some embodiments, the repository tool can support custom analyte display data visualization. When a patient returns a custom analyte display, the repository tool can be used to download the device data and further investigate the device. In some embodiments, the tech support system 420 can include a transmitter download tool. When a patient returns a transmitter for investigation, the transmitter can be downloaded using this tool and the data can be visualized as a data table using a database viewer, for further investigation.

Multiple Copies

In some embodiments, the cloud computing architecture may receive and store multiple copies of the same data stream for various purposes including providing automatic or semi-automatic tech support, issue detection and resolution. As described herein, in some embodiments, the real time server 408 can receive real time data from the display devices 404, more frequently than the BDC 412 receives data from the display devices 404. For example, the real time server 408 can receive real time data from the display device 404a every hour automatically via a wireless connection; the BDC 412 can receive bulk data from the display device 404b when the patient initiates uploading bulk data. A copy of bulk data can be stored in the BDD 414 for a longer time than the same copy stored in the BDC 412. In some embodiments, various storage durations for various copies of the same data stream can be designated and executed to accomplish different objectives, for example, to comply with a mandated "keep data" order within the cloud computing system 410. While not shown, the cloud computing system 410 can include an IT archive server, which can store data for which there is a mandated "keep data" order longer than the storage durations among other components of the cloud computing system 410. As described, multiple copies within the cloud computing system 410 (which may be included for objectives other than providing tech support) can nevertheless be utilized to automatically identify and resolve technical issues. For example, in some embodiments, multiple copies are stored in the IT archive server to comply with quality requirements "keep data" durations. These multiple copies may be recalled, analyzed and compared with other copies of the same data stream in order to identify or resolve technical issues.

Proactive detection, identification and analysis of technical issues (within one patient's devices or within a multitudes of patients' devices) can be accomplished by automatically analyzing the output of the medical device provider's systems and services that may not be specifically directed to providing technical support. In some embodiments of system 300, retrospective reporting may be provided to allow patients and their caregivers to view patient's data and metrics associated with the patient's data. In some embodiments, if the tech support system 420 detects a failure, the patient or patient's caregiver can be provided with questionnaires in addition to retrospective reporting. In some embodiments, the questionnaires may be in the form where answers are collected by receiving inputs and selections via drop down menus, radio buttons or other forms where limited free text is allowed. Collecting data in this form allows for expedient analysis, for example, via running population or data analytics.

In some embodiments, the patient may be presented with general or real time information on the tech support system 420 or the tech support personnel 434. For example, the patient can, by navigating through a menu driven application, be informed as to a current estimate of tech support wait/hold times if the patient were to speak with a tech support technician. Additionally, comparison estimated wait times of automated troubleshooting option can be presented. The wait time estimates can be determined from system-wide historical analysis of tech support data by time of day, week, month, etc. In some embodiments, the wait time estimates can be provided to the patient after the patient has provided information and data associated with her technical issue. The provided wait time estimates can be informed by or adjusted by the technical issue data entered into the system.

In some embodiments, the analyte sensor application 330 or similar application used by the patient can be equipped with a menu option for locating physical stores where devices of a medical device company or replacement parts are sold. In some embodiments, the patient can place an order for medical device products or replacement parts by interacting with the analyte sensor application 330. The physical stores can allow inventory availability checks, receipt of orders, holding of and in-store pick-up of products.

In some embodiments, when automatically processing a patient's request for sensor replacement and before an automatic replacement order is booked, one or more anti-fraud algorithms can be utilized to determine whether the request for sensor replacement is genuine, due to user error or is a result of a real sensor failure.

Tech Support Documentation

Medical device providers, who offer the products and systems described herein may have to contend with laborious documentation following a call to their tech support centers. For example, after a patient places a call to a medical device tech support center, and a tech support technician has resolved the patient's issue, the technician or other personnel may have to document the call by manually entering information associated with the call. Manual entry of the information associated with the call, for example, can include recording the technical issue the patient faced, the troubleshooting script the technician chose, the questions the technician presented to the patient, the patient's responses, information collected regarding the context of the patient's call, the patient's hardware, the patient's software and other relevant data. The tech support personnel generate a report based on the gathered information. The report may be transmitted to other departments within the medical device provider based on various objectives. Those departments may in turn audit the report based on various objectives before formally concluding a documentation process associated with a patient technical support call. For example, quality assurance department may receive and audit the report to determine whether the information gathered in the report is satisfactory for the purpose of improving products or service quality. The documentation process may be concluded after the various departments within the medical device provider have audited and approved the report. In some cases, the report is sent back to the tech support personnel to gather additional data as required by various departments within the medical device provider. Consequently, the documentation obligations associated with a patient's call or email to a tech support center are considerable. The systems and methods described herein can relieve such documentation obligations by automating the gathering of the data, and generation reports or documentation associated with a call to tech support.

In some embodiments, the analyte sensor application 330 can be configured with various tabs presented to the patient when the patient attempts to troubleshoot an issue using the analyte sensor application 330. Clicking the tabs can guide the patient through a decision tree for resolving the technical issue. Clicking on some options or tabs can trigger the analyte sensor application 330 to alert the tech support system 420 to take action regarding the patient's technical issue. The tech support server 422, or if tech support personnel 434 have been engaged, can text or otherwise push messages to the analyte sensor application 330 to be displayed to the patient informing them of the progress of the troubleshooting of their issue.

Remote Control of Medical Device

In some embodiments, the tech support system 420 or the tech support personnel 434, automatically, or in response to a patient's request, can establish remote control of a patient's medical devices (e.g., display devices 404 or CGM 402) in order to provide automated or semi-automated tech support. By establishing one or more remote control events, the tech support system 420 or the tech support personnel 434 can accomplish tasks associated with diagnosis and resolving of patient's technical issues. For example, a remote control event can include status query, self-diagnostic troubleshooting algorithms, reading and writing control data into and out of the patient's medical devices, modifying device parameters and other control events. In some embodiments, a remote control event is transmitted from the tech support server 422 to a patient's medical device, for example to a display device 404. As described earlier, the display device 404 may be a smart phone, smart wearable device or a custom analyte display device. The remote control event can include algorithms, software instructions or scripts for running one or more tests, troubleshooting scripts, diagnostic tools, or similar tech-support-related algorithms to be operated on the patient's medical devices (e.g., the CGM 402 or display devices 404). The remote control event can include an internet transaction, notification, text message or other interactions. In some embodiments, the display device 404 can receive and store the remote control event instructions until such time as specified by the remote control event. The control event may contain algorithms to be operated on the CGM 402, the display 404, both, or other patient's medical devices. In some cases, the remote control event contains software instructions or algorithms to be executed in the event of detection of a present or future event or to be repeated under pre-defined conditions. A trigger event for execution of a control event can include detection of a value of a parameter within the patient's medical devices, or medical device parameters surpassing a threshold range or staying within a thresholds range. In some cases, the remote control event may be executed immediately upon receipt from the tech support system 420 or the tech support personnel 434. In other cases, the remote control event may be programmed to run over a period of one or more cycles (e.g., the cycles can be defined as cycles of interaction period between the CGM 402 and the display devices 404). In some cases, upon execution of a remote control event, the obtained results, values, parameters, and/or device observations can be transmitted to the tech support system 420 for further analysis or action. The described remote control techniques can be invoked as part of automatic diagnosis and troubleshooting of technical issues in error tickets. Appropriate notifications in the form of visual or audio alerts can accompany the execution and operation of a remote control event.

Example Embodiments of Tech Support Data Flow

In some embodiments of the tech support system 420, the tech support server 422 can further communicate with a regulatory incident record database 430. As described herein, some technical issues discovered by or reported to the medical device provider trigger an obligation of recording the incident in a database, and in some cases, reporting the incident to governmental regulatory bodies, such as the FDA. For this purpose, a regulatory incident record database 430 can be created for storing technical issues and associated data for which a government regulatory recording or reporting obligation exists. The tech support system 420 can automatically update the regulatory incident record database 430.

In some embodiments, when a patient encounters an "error condition encountered," an error flag is transmitted to the receivers 404a and 404b via wired or wireless communication. In some cases, the CGM 402 or its transmitter (e.g. embedded transmitter) can generate a device-triggered error flag. The patient may choose to report further information about the incident or provide other contextual information to be included with the error flag. The receivers 404a and/or 404b can also add additional information to the error flag. As described above, the receivers 404a and/or 404b can communicate with the tech support server 422 via a wired or wireless connection providing the error flag to the tech support server 422.

The tech support server 422 can include software or hardware modules to automatically or semi-automatically: record an incident information embedded in an error flag by accessing and writing into one or more relevant databases; diagnose the issues giving rise to the error flag; and determine an appropriate resolution or response to the error flag.

For example, in some embodiments, automatic diagnosis and resolution of the errors giving rise to the error flag can include matching an error code embedded in the error flag against a database of previously known issues and their associated known resolutions. For example in some cases, the error flag can contain an error code as well as information about the receiver registering the error code which make evident the condition for a known error where an app running in the background of the receiver device causes issues with the app handling the operations of the CGM 402. A known resolution can be identified by suggesting a swipe/kill the conflicting app. In other cases, the error code embedded in the error flag can be linked to a bad sensor. Subsequently, ordering a replacement sensor can be identified as the resolution of the issue.

Semi-Automatic Diagnosis/Resolution

In some embodiments, the tech support server 422 may do preprocessing and analysis on the error ticket before subsequently sending the error ticket information and any analysis to technical support personnel 434. In some embodiments, if the tech support server 422 cannot resolve the patient's technical issue automatically, it may forward the error ticket to tech support personnel 434 along with preprocessing and analysis to assist them in determining the cause and resolution of a patient's technical issue. The tech support server 422 can utilize machine learning, decision control logic or other techniques to determine if the diagnosis and resolution of an issue is better delegated to a tech support personnel 434. In some embodiments, the tech personnel 434 can partially handle identification and resolution of a patient's technical issue and hand off some operations to the tech support system 420.

HIPAA Compliance

While FIG. 4 shows the tech support server 422 as a separate server than the BDD 414, in other embodiments, the tech support server 422 can be an integral part of the BDD 414 to expedite diagnosis or resolution of patient's technical issues. In other embodiments, the tech support server 422 can be a separate server from the BDD 414 as shown in FIG. 4.

Advantages of separating the tech support server 422 from the BDD 414 can include an ability to operate the two databases under separate FDA classifications. For example, if the BDD 414 is deemed a Class III device, in some embodiments, the tech support server 422 can be operated as a Class I or Class II device by controlling the data routed to the tech support server 422. In some embodiments, it may be advantageous to have one or more tech support servers 422 with different FDA classifications. In that instance, one tech support server 422 with the same FDA classification as the BDD 414 can be embedded in the BDD 414 and handle patient's technical issues and data that are appropriate for the FDA classification of the BDD 414. Other issues and data appropriate to other FDA classifications can be routed to an alternate tech support server 422. By automatic, intelligent routing of patient's technical issues to appropriate tech support server 422, diagnosis and resolution of the issues can be performed expeditiously and the resources of the cloud computing architecture 410 can be preserved.

Figure 5A:
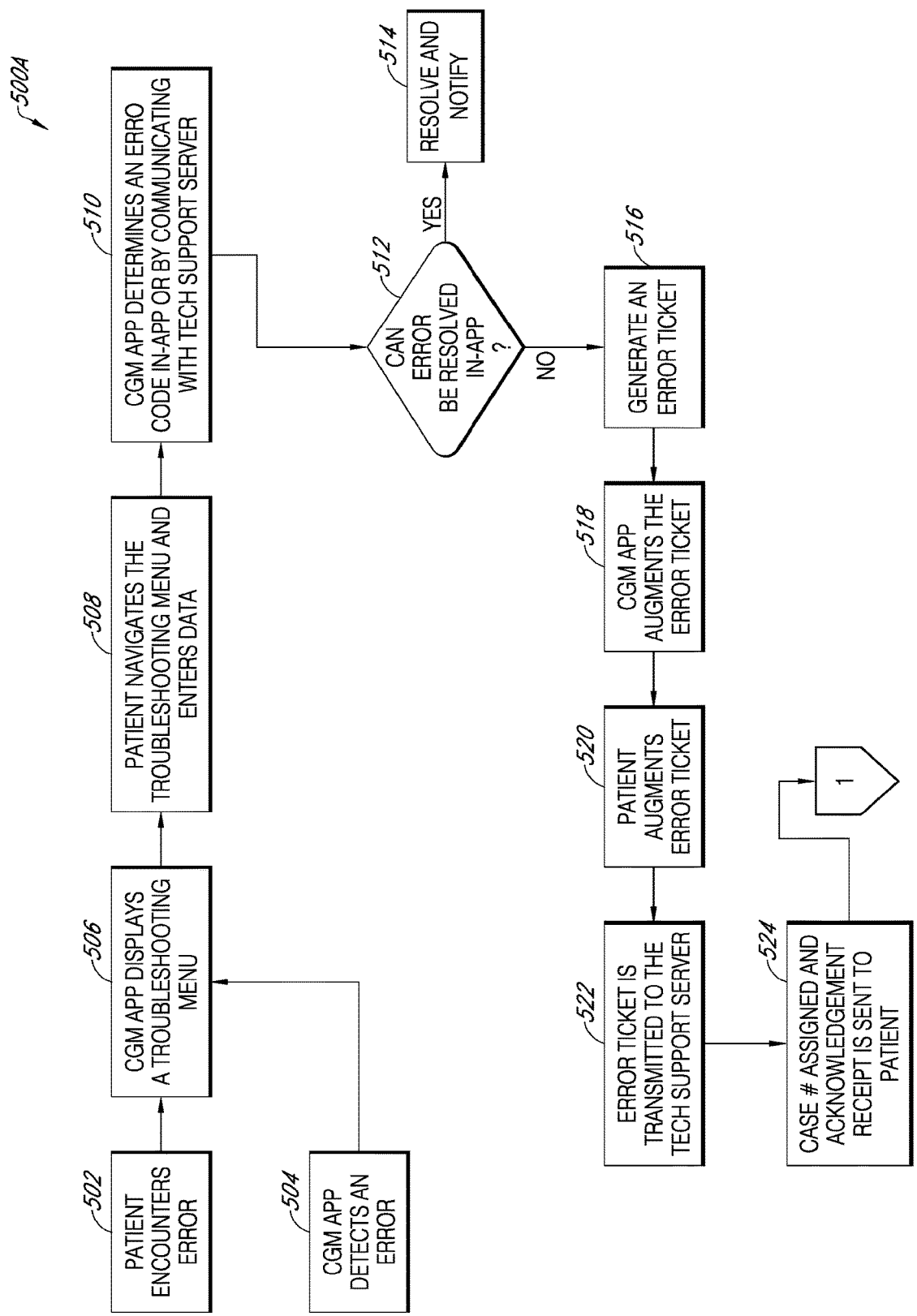
FIGS. 5A and 5B illustrate a flow chart of an example process to provide automated or semi-automated technical support in accordance with embodiments of the present technology.
Figure 5B:
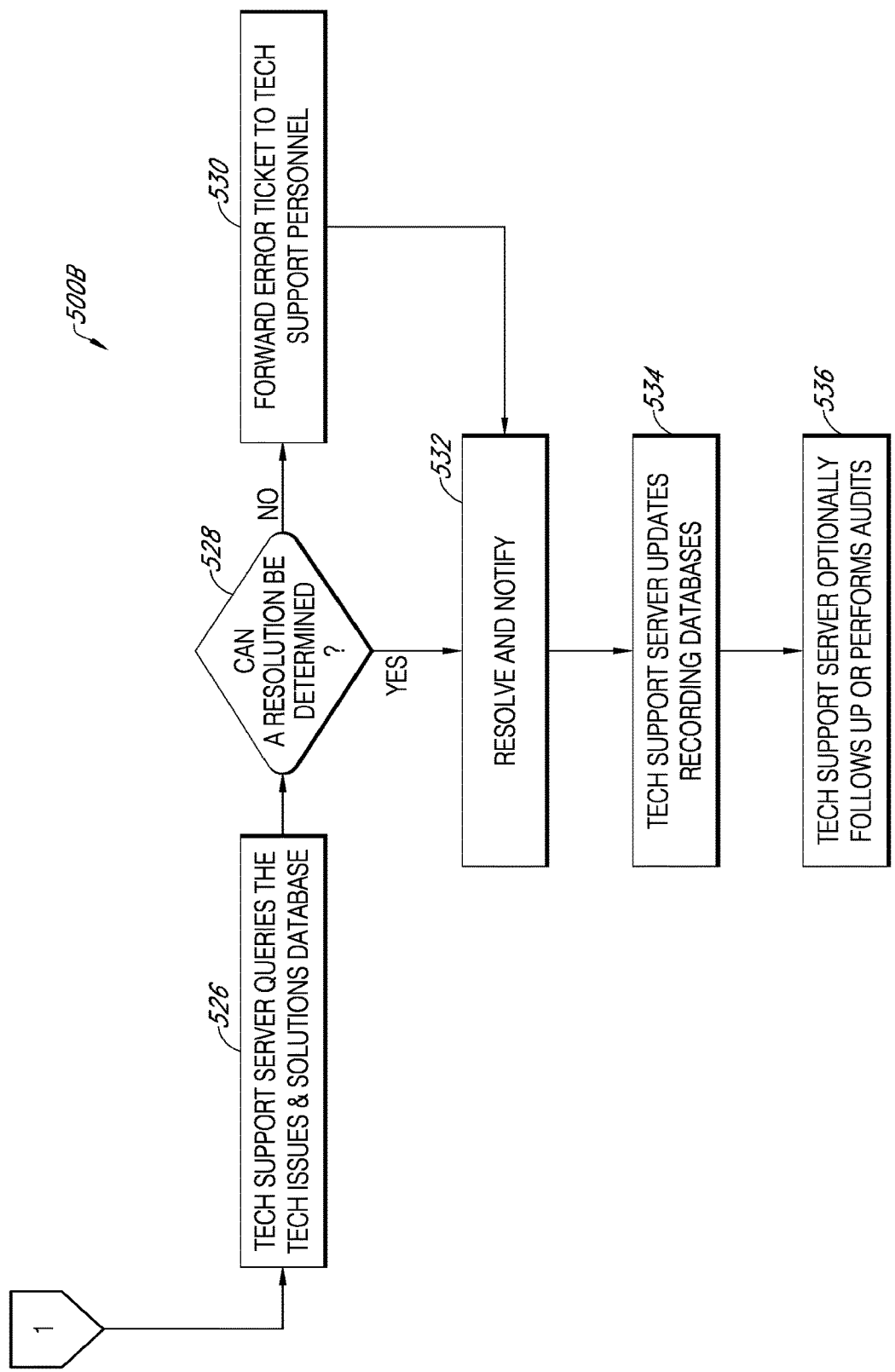

FIGS. 5A and 5B illustrate a flow chart 500A-B of an example process to provide automated or semi-automated technical support in accordance with embodiments of the present technology.

The process starts at block 502 or block 504 as the patient encounters an error or the analyte sensor application 330 detects an error. At block 506, the analyte sensor application 330 presents a troubleshooting menu (or the patient activates a troubleshooting menu within the analyte sensor application 330). At block 508, the patient navigates the troubleshooting menu and enters data relevant to the encountered issue. At block 510, the analyte sensor application 330 determines an error code applicable to the issue encountered. The determination of an error code, can happen within the analyte sensor application 330 or can be obtained from the tech support system 420. At block 512, it is determined whether the encountered issue can be resolved locally within the analyte sensor application 330. If yes, the process moves to block 514, where the issue is resolved and the results are reported to the patient, for example by displaying a notification on the display device 404. If no, the process moves to block 516 where an error ticket is generated. The process then moves to block 518. The analyte sensor application 330 can augment the error ticket with contextual or other additional data relevant to the error code associated with the issue encountered. In some embodiments, the analyte sensor application 330 can run algorithms associated with an error code to collect data relevant to that error code. The process then moves to block 520. The patient can augment the error ticket with annotations, contextual data, comments, historical data, or any other information relevant to the technical issue encountered. The process then moves to block 522. The error ticket is transmitted to the tech support system 420. As described, in some embodiments, the error ticket is transmitted to a tech support server 422 within the tech support system 420. The process moves to block 524. In some embodiments, a case number can be assigned to the error ticket and an acknowledgement receipt can be sent to the patient via analyte sensor application 330 or display device 404.

The process continues to block 526 (illustrated in FIG. 5B). The tech support server 422 can query the tech issues & solutions database 432 based on the error code and other information in the error ticket. The tech support server 422 can run searches in the tech issues & solutions database 432 and recall one or more applicable troubleshooting algorithms. In some embodiments, the troubleshooting algorithms may contain rankings or scores based on their applicability and prior favorable performance for troubleshooting a given error code. The tech support server 422 can utilize such rankings to identify a best-match troubleshooting algorithm. The process moves to bock 528, where it is decided whether a resolution to the technical issues in the error ticket can be determined. If no, the process moves to block 530 where the error ticket and any additional information appended by the tech support server 422 can be forwarded, for example via email, on screen chat, text alert, or other communication means, to the tech support personnel operating the tech support personnel computing system 434. The tech support personnel can take over handling of the error ticket, resolve the issue and notify the patient. In some embodiments, the tech support personnel can also manually handle any additional recording or processing steps associated with the resolution of an error ticket, thereby overwriting the automatic process of 500A-B.

If the tech support system 420 can determine a resolution of the technical issue associated with the error ticket, the process moves to block 532. The tech support system 420 resolves the technical issue in the error ticket and notifies the patient. The process moves to block 534 where the tech support server updates one or more recording databases of a medical device provider operating the patient's medical devices. As discussed, these recoding databases can include a tech issues & solutions database 432, patient records 424, product records 426, accounting 428 and regulatory records 430. The process optionally moves to block 536 where the tech support system 420 automatically follows up with the patient after a predetermined time (e.g., within 24 hours, or a week). The length of the period of time for follow up can be informed by the error code, type and severity of the issue encountered and any medical exigencies associated with a given error code. As described in some embodiments, the tech support personnel operating the tech support personnel computing system 434, can optionally override the automatic process 500A-500B at some stage. In some cases, when the tech support personnel resolve an issue, which was not resolved by the automatic process 500A-B, the tech support personnel can re-engage the process 500A-B, by handing off patient notification and subsequent documentation and recording to the block 532 and/or 534 of the process 500A-B. In some embodiments, the tech support personnel can handle the notification and documentation tasks manually. In such cases, the process 500A-B can perform audits and send reminders to the tech support personnel regarding these tasks.

Example Use Cases of Automated or Semi-Automated Tech Support

When a patient experiences a device failure, the analyte sensor application 330 can generate an error ticket as described herein and transmit the error ticket to the tech support system 420. In some embodiments, the tech support server 422 can receive and analyze the error ticket. The tech support server 422 can transmit an acknowledgment response to the display device 404. The acknowledgment response can include an appropriate customer service message (e.g., a message of apology for the device failure, an explanation that the issue will further be investigated, the timeframe within which the medical device provider will reach back to the patient with a resolution and any instructions or remedial measures concerning what the patient may have to do in the meanwhile). The acknowledgment response initially sent to the display device 404 can be generated based on the error code associated with the error ticket transmitted to the tech support server 422.

Additionally, when the patient experiences a sensor failure, a sensor failure screen can appear on the display device 404 along with a "report problem/request sensor replacement" button displayed on the display device 404. In some embodiments, when the patient clicks on the report button, she is directed to a website, where she can be presented with one or more questionnaire forms containing questions associated with troubleshooting a sensor failure error and potential sensor replacement order. When the patient submits her responses, they can be transmitted to the tech support server 422 of the tech support system 420. In some embodiments, the questionnaire form may be presented to the patient as a menu option within the analyte sensor application 330, such that the patient does not have to visit a webpage. In some embodiments, a case number can be associated with the error ticket. The patient or the tech support personnel 434 can track or follow up on the status of the error ticket using the case number.

In some embodiments, the contents of the error ticket can be turned into an email and forwarded to the tech support personnel 434. In a semi-automated system, the tech support personnel 434 can manually perform the logging, recording and reporting that may be associated with the patient's request for tech support. In automated embodiments, as described herein, the logging, recording and reporting can be performed by the tech support system 420, without intervention from the tech personnel 434. In other embodiments, as described herein, a combination of automated and semi-automated implementations can be used where the tech support personnel intervene in some circumstances and not in others.

If sending a replacement sensor is identified as a resolution of a patient's technical issue, the tech support server 422 (or tech personnel 434) can book a replacement sensor to be shipped to the patient. By consulting the patient's records, the tech support server 422 can determine the delivery and shipment speed appropriate for the patient based on the urgency of the need to deliver a new replacement sensor. The patient may be notified via an email message, SMS, on-screen alert, or other means of communication. The patient can also be provided with shipment tracking information. In some embodiments, the tech support server 422, before ordering a replacement sensor, can check the patient records 424 to determine whether multiple sensors have been ordered within a short period of time. If the patient records 424 show that the patient has ordered multiple sensors within a short period of time, the tech support server 422 can flag the error ticket and request intervention from the tech support personnel 434, by sending an email, on-screen alert or other means of communication. The tech support server 422 can also send a notification message to the patient alerting her that multiple sensor replacements have been detected and a tech support technician will contact them.

Patient's medical devices, which are part of the analyte monitoring systems and architecture (e.g., sensors, receivers, etc.), can be configured to report any failure to the tech support system 420, for example, by generating and transmitting error tickets as described herein. In some embodiments, prior to transmission of an error ticket, the patient or patient's devices can augment an error ticket with appropriate contextual or additional data to assist in resolution of the issues. In some embodiments, the tech support system 420, upon receipt and analysis of an error ticket, may query the device or the patient associated with the error ticket for additional data to assist in resolving the technical issues. Depending on the failure reported, the tech support system 420 can take a number of actions, including confirming failure, sending acknowledgement receipts, beginning the process of product return or replacement, logging and recording the issue in appropriate databases including the patient records 424, product records 426, accounting 428 or regulatory records 430.

In some cases, the patient can report inaccuracies in sensor readings. The patient can compare the sensor readings reported on the display devices 404 to a manual reading from a self-monitoring blood glucose (SMBG) device. If the readings between the devices contain discrepancies, the patient can report an "inaccuracy" technical issue. The analyte sensor application 330 running on the display device 404 can present the patient with one or more menu options directed to troubleshooting sensor inaccuracies. The patient can request "inaccuracy analysis" for a given time period by interacting with menu options within the analyte sensor application 330. In some embodiments, if no time period is specified, the inaccuracy analysis can be performed from the beginning of a sensor reading session (a sensor reading session can, for example, start from when the patient clicks "start sensor" within a menu of the analyte sensor application 330). The analyte sensor application 330 can collect information from the patient, interact with the patient through questions/answers forms and present the patient with analysis and diagnosis regarding sensor inaccuracies. For example, the analyte sensor application 330 can present the difference between values obtained from a SMBG device (during one or more calibration event) and the CGM 402. The user can be prompted to enter data relevant to inaccuracy analysis, for example, the brand name of the SMBG and the type of calibration strip used. As described herein, if the analyte sensor application 330 determines that the perceived inaccuracy is within the acceptable tolerances of the CGM 402, it can present the patient with user manual, clinical trial data or other authoritative sources of information to reassure the patient of the correct operation of her medical device. If the patient or the analyte sensor application 330 determines that the sensor readings are inaccurate, an error ticket can be generated and transmitted to the tech support system 420 as described herein.

An example of automatic failure detection and resolution includes automatic detection of speaker failure. In the context of medical device, audible devices and components of the device can be important because the patients or the caregivers may rely on their correct operation to hear potentially life-saving or important medical alarms. Sometimes the patient inadvertently silences the speaker on their display device 404. If the patient uses a mobile device, such as a smart phone, as their display 404, it may be likely that the patient silences the speaker on their mobile phone from time to time, for example when attending a meeting or a public speaking event. The patient may not realize that potentially important medical alarms may also be silenced. In other cases, the speaker or other auditory devices within an analyte monitoring system may experience a mechanical, electrical or other hardware failure. The failure or inadvertent silencing of auditory devices within a medical device can be detrimental to patient's health. In some embodiments, the analyte sensor application 330, or other hardware or software within the analyte monitoring system can periodically check the operation of auditory components of the system 300.

Figure 6A:
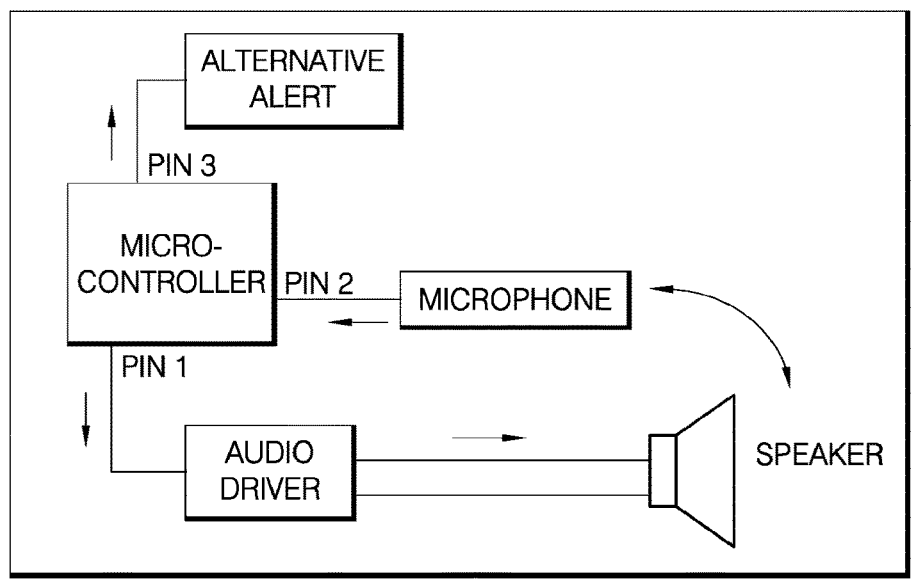
FIGS. 6A and 6B illustrate aspects of example systems for automatic failure detection.
Figure 6B:
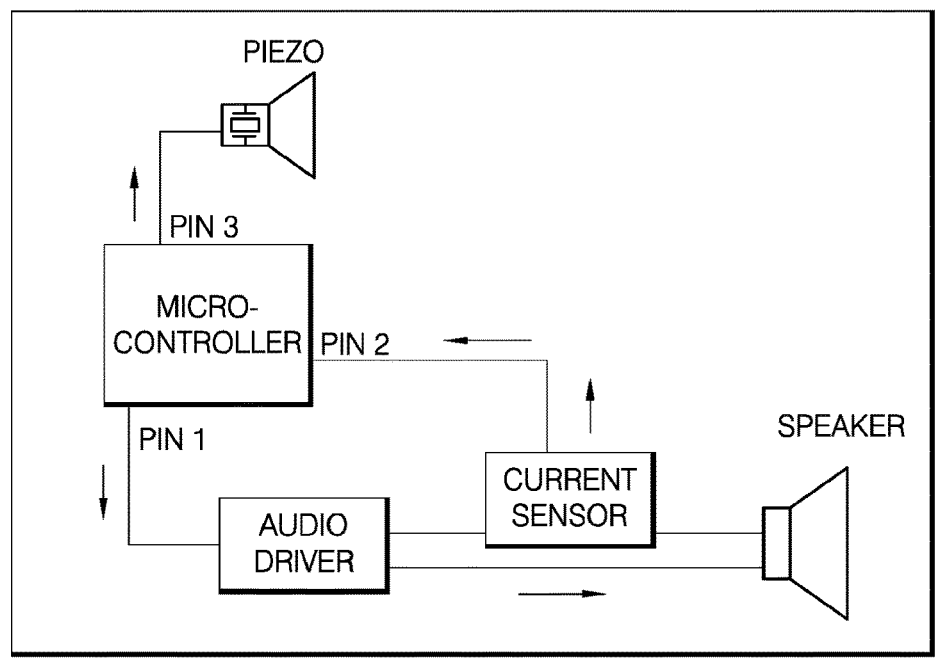

An example system of checking the correct operation of auditory devices is illustrated in FIGS. 6A and 6B. In some embodiments of the display devices 404, if a custom analyte monitoring device is used, the custom device can utilize a microphone or Hall Effect current sensor as a feedback element. By applying a control feedback loop, speaker failure can be detected. If such failure is detected, alerts can be issued using alternate methods.

The control loop can verify a speaker output during the times in which the speaker auditory output is expected. If the speaker has failed, the control loop senses no feedback current. Automatic alternative alert methods can be employed to ensure delivery of alerts. Alternative alerts can include small alternate piezo, an aggressive mechanical vibration, or a visual alert, for example, a text or other alert sent to the patient's phone connected by BLE.

The approach outlined above and illustrated in FIGS. 6A-6B can allow for automatic diagnosis of the speaker failure, without human intervention. The control loop's low profile components can be added to custom analyte monitoring devices without unduly taking up valuable space within the monitoring device.

Similar techniques (control loops, feedback sensing, control electronics, sensors, etc.) implemented in hardware or software can be used to automatically detect similar component failures (in addition to detecting auditory device failure) within the devices of the analyte monitoring system 300.

An example of automatic failure detection and resolution/mitigation includes automatic detection of data gaps. Data gaps in analyte data may have an adverse effect on the operations and functioning of the analyte monitoring system 300. The system relies on the (historical and current) analyte data to offer visuals, alerts and reminders to help the patient manage her health. Some data gaps can be caused by inadvertent shut down of the analyte sensor application 330. For example, a system or memory reset on the display device 404 or a Bluetooth server crash can cause inadvertent shut down of the analyte sensor application 330 and subsequent loss of data leading to data gaps. In some embodiments, the tech support system 420 can track the activity of its connected devices and their associated analyte sensor applications 330. If it is detected that an analyte sensor application 330 of a patient is offline, the tech support system 420 can send a silent push message to wake up the analyte sensor application. In some cases, the tech support system 420 can detect data gaps by comparison between copies of the same streams of data routed to different databases (e.g., the real time data routed to the real time server 408 or the bulk data routed to the BDC 412). Upon determining a discrepancy between the data stream copies stored in different servers, the tech support system 420 can send a status query or a silent push message to wake up the analyte sensor application 330. In some embodiments, the tech support system 420 can gather information related to the data gaps (e.g., whether the gap was caused by a memory reset, a Bluetooth server crash, timing of the data gap—whether night time or day time, etc.) The tech support system 420 can identify patterns in sources of data gaps and accordingly adjust the frequency and timing of sending silent pushes or wake up calls to various analyte sensor applications 330. For example, the tech support system 420 can determine that data gaps due to memory reset are more frequent for some patients during nighttime. The tech support system 430 can increase the frequency of silent pushes or wake up messages for those patients during nighttime.

An example of automatic tech support application of the embodiments described herein can include automatic ordering (or reordering) of CGM 402 or other parts within the analyte sensor system 308. In some embodiments of the analyte monitoring system 300, the CGM 402 or parts therein (e.g., the parts within the analyte sensor system 308 of FIG. 3B such as the sensor electronics) may need to be replaced after a predetermined period of use. The initial start date of new parts can be determined and stored when the cloud computing architecture 410 first receives an upload from a patient's newly installed device, or newly replaced part. The tech support system 420 can track the age of various components of the analyte monitoring system 300 or the analyte sensor system 308. The tech support system 420 can be configured to automatically check its relevant databases on the components age-out date (or some predetermined time prior to age-out date) to determine whether a replacement part has been scheduled for shipping. If yes, the tech support system 420 can notify the patient of the scheduled shipment and associated information, such as expected delivery date, tracking number and billing information. If no replacement part has been scheduled as expected, the tech support system 420 can notify the patient accordingly and request authorization for scheduling and shipment of replacement parts.

Figure 7:
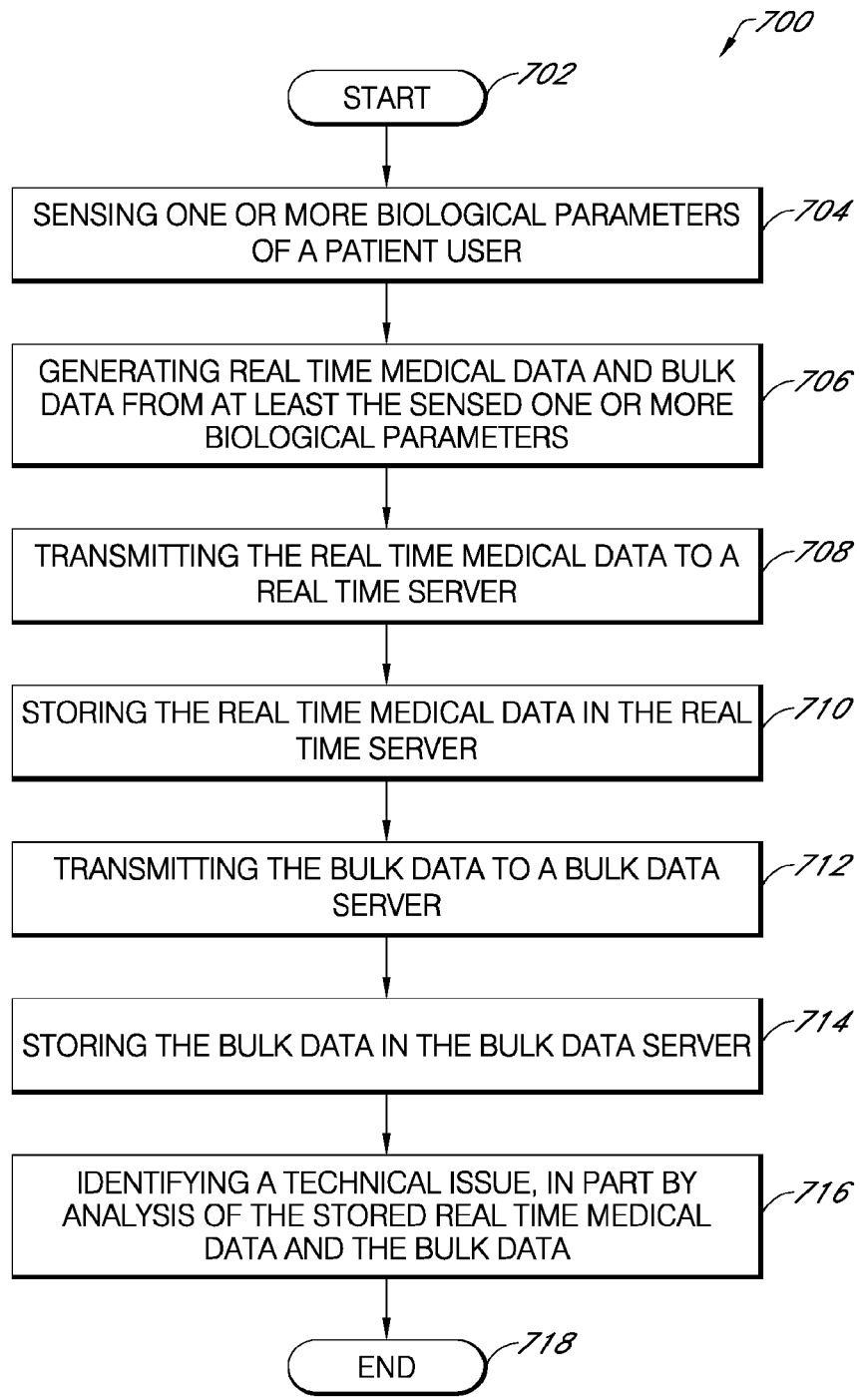
FIG. 7 illustrates a flow chart of an example to provide automated or semi-automated technical support in accordance with embodiments of the present technology.

FIG. 7 illustrates a flow chart 700 of an example to provide automated or semi-automated technical support in accordance with embodiments of the present technology. The process starts at block 702. At block 704, the process continues by sensing one or more biological parameters of a patient user. At block 706, the process continues by generating real time medical data and bulk data from at least the sensed one or more biological parameters. At block 708, the process continues by transmitting the real time medical data to a real time server. At block 710, the process continues by storing the real time medical data in the real time server. At block 712, the process continues by transmitting the bulk data to a bulk data server. At block 714, the process continues by storing the bulk data in the bulk data server. At block 716, the process continues by identifying a technical issue, in part by analysis of the stored real time medical data and the bulk data. The process ends at the block 718.

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g., smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

In this document, the terms "computer program medium" and "computer usable medium" and "computer readable medium", as well as variations thereof, are used to generally refer to transitory or non-transitory media such as, for example, main memory, storage unit interface, removable storage media, and/or channel. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module or a processor thereof or connected thereto to perform features or functions of the present disclosure as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system, comprising:
   an analyte sensor device configured to generate analyte data over a time period and transmit the analyte data to a display device;
   the display device configured to execute an analyte sensor application to:
   identify a gap in the analyte data during the time period;
   generate an error ticket indicative of the gap in the analyte data;
   append, to the error ticket, augmentation data relevant to the gap in the analyte data; and
   transmit the error ticket and the augmentation data to a technical support system;
   the technical support system configured to:
   automatically analyze the error ticket and the augmentation data;
   automatically identify, based on the analyzing, a software application conflict as a cause of the gap in the analyte data; and
   automatically send an over-the-air software update to the display device to be executed by the display device for resolving the software application conflict; and
   the display device further configured to:
   receive the over-the-air software update from the technical support system;
   apply the over-the-air software update to the display device; and
   display an alert indicative of the software application conflict and the over-the-air software update applied to resolve the software application conflict.

2. The system of claim 1, wherein the augmentation data indicates the time period in which the gap was detected.

3. The system of claim 1, wherein the display device is configured to display an alert indicative of the gap identified in the analyte data.

4. The system of claim 1, wherein the alert indicates a portion of the time period corresponding to the gap.

5. The system of claim 1, wherein the technical support system is further configured to:
   identify a pattern of software application conflicts based on the error ticket, the augmented data, and one or more other error tickets and corresponding augmented data received prior to receiving the error ticket; and
   determine the over-the-air software update based on the identified pattern.

6. The system of claim 1, wherein the display device is further configured to:
   generate a prompt requesting a patient permission to send the error ticket;
   receive the patient permission in response to the prompt; and
   append the patient permission to the error ticket for transmission to the tech support system.

7. The system of claim 1, wherein:
   the technical support system is further configured to determine a user course of action to reduce subsequent occurrences of the software application conflict; and
   the display device is further configured to:
   receive an indication of the user course of action from the technical support system; and
   display a prompt identifying the user course of action.

8. A method, comprising:
   identifying, by a display device, a gap in analyte data corresponding to a time period;
   generating, by the display device, an error ticket indicative of the gap in the analyte data;
   appending, by the display device, to the error ticket, augmentation data relevant to the gap in the analyte data; and
   transmitting, by the display device, the error ticket and the augmentation data to a technical support system;
   automatically analyzing, by the technical support system, the error ticket and the augmentation data;
   automatically identifying, by the technical support system, based on the analyzing, a software application conflict as a cause of the gap in the analyte data;
   automatically sending, by the technical support system, an over-the-air software update to the display device to be executed by the display device for resolving the software application conflict;
   receiving, by the display device, the over-the-air software update from the technical support system;

applying, by the display device, the over-the-air software update; and displaying, by the display device, an alert indicative of the software application conflict and the over-the-air software update applied to resolve the software application conflict.

9. The method of claim 8, wherein the augmentation data indicates the time period in which the gap was detected.

10. The method of claim 8, further comprising displaying, by the display device, an alert indicative of the gap identified in the analyte data.

11. The method of claim 8, wherein the alert indicates a portion of the time period corresponding to the gap.

12. The method of claim 8, further comprising identifying, by the technical support system, a pattern of software application conflicts based on the error ticket, the augmented data, and one or more other error tickets and corresponding augmented data received prior to receiving the error ticket; and determining, by the technical support system, the over-the-air software update based on the identified pattern.

13. The method of claim 8, further comprising:

generating a prompt requesting a patient permission to send the error ticket;

receiving the patient permission in response to the prompt;

appending the patient permission to the error ticket for transmission to the tech support system.

14. The method of claim 8, further comprising:

determining, by the technical support system, a user course of action to reduce subsequent occurrences of the software application conflict;

receiving, by the display device, an indication of the user course of action from the technical support system; and displaying, by the display device, a prompt identifying the user course of action.

15. At least one non-transitory computer readable medium having instructions stored thereon that, when executed by at least one processor, cause the at least one processor to perform a method comprising:

identifying a gap in analyte data corresponding to a time period;

generating an error ticket indicative of the gap in the analyte data;

appending to the error ticket, augmentation data relevant to the gap in the analyte data;

transmitting the error ticket and the augmentation data to a technical support system;

automatically analyzing the error ticket and the augmentation data;

automatically identifying, based on the analyzing, a software application conflict as a cause of the gap in the analyte data;

automatically sending an over-the-air software update to a display device to be executed by the display device for resolving the software application conflict;

receiving the over-the-air software update from the technical support system;

applying the over-the-air software update to the display device; and displaying an alert indicative of the software application conflict and the over-the-air software update applied to resolve the software application conflict.

16. The at least one non-transitory computer readable medium of claim 15, wherein the augmentation data indicates the time period in which the gap was detected.

17. The at least one non-transitory computer readable medium of claim 15, wherein the method further comprises displaying an alert indicative of the gap identified in the analyte data.

* * * * *